United States Patent [19]

Beck et al.

[11] Patent Number: 5,075,326

[45] Date of Patent: Dec. 24, 1991

[54] PESTICIDAL 4-HALOGENO-5-NITROTHIAZOLES

[75] Inventors: Gunther Beck, Leverkusen; Wilhelm Brandes, Leichlingen; Stefan Dutzmann, Duesseldorf; Wilfried Paulus, Krefeld, all of Fed. Rep. of Germany

[73] Assignee: Bayer Aktiengesellschaft, Leverkusen, Fed. Rep. of Germany

[21] Appl. No.: 513,745

[22] Filed: Apr. 24, 1990

Related U.S. Application Data

[62] Division of Ser. No. 378,894, Jul. 12, 1989, Pat. No. 4,962,102.

[30] Foreign Application Priority Data

Jul. 20, 1988 [DE] Fed. Rep. of Germany ....... 3824520
Dec. 21, 1988 [DE] Fed. Rep. of Germany ....... 3842970

[51] Int. Cl.$^5$ .................... C07D 277/58; A01N 43/78
[52] U.S. Cl. ..................................... 514/369; 548/184
[58] Field of Search ................. 548/184; 514/369

[56] References Cited

U.S. PATENT DOCUMENTS 4,962,102 10/1990 Beck ..................................... 514/212

FOREIGN PATENT DOCUMENTS 2168182 10/1973 France ................................. 548/181
68479 4/1986 Japan ..................................... 548/191

Primary Examiner—Robert Gerstl

Attorney, Agent, or Firm—Sprung Horn Kramer & Woods

[57] ABSTRACT

Fungicidal 4-halogeno-5-nitrothiazoles of the formula

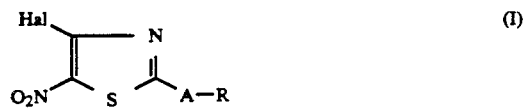

(I)

in which
Hal represents halogen,
A represents O, S, SO, SO$_2$ or N—R$^1$, wherein
  R and R$^1$ each independently is hydrogen or an organic radical, or together with
  N form a heterocyclic ring,
with the exception that R is not hydrogen if A represents SO or SO$_2$.

Compounds of the formula

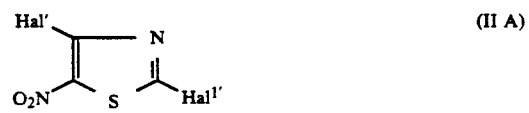

(II A)

in which
Hal' and Hal" independently of one another represent chlorine, iodine or fluorine, with the proviso that the two Hals may not simultaneously be chlorine,
are also effective in protecting industrial materials against microbes.

11 Claims, No Drawings

PESTICIDAL 4-HALOGENO-5-NITROTHIAZOLES

This is a division of application Ser. No. 378,894, filed July 12, 1989, now U.S. Pat. No. 4,962,102.

The present invention relates to new 4-halogeno-5-nitrothiazole derivatives, several processes for their preparation and their use as agents for combating pests, and some new intermediate products.

It is known that thiazoles which are substituted, for example, by hydroxyphenoxy are used in medicine for the treatment of tumors (compare WO 88/00,944).

It is furthermore known that 2,4-dichloro-5-nitrothiazole has a microbicidal action, above all a fungicidal action, in plant protection (compare DE-OS (German Published Specification) 3,518,520).

Thiazole derivatives, such as, for example, 4,5-dichloro-2-propinyloxy-thiazole, are also known as synergists (compare DE-OS (German Published Specification) 3,030,661).

It is furthermore known that certain substituted thiazoles, such as, for example, 4-benzimidazol-2-yl-thiazole (thiabendazol), are used as fungicides for the protection of materials (cf., for example, R. Wegler "Chemie der Pflanzenschutz- und Schädlingsbekampfungsmittel" [Chemistry of Plant Protection Agents and Pesticides], Vol. 2, p. 124, and Vol. 3, p. 292; Springer Verlag, Berlin, Heidelberg, N.Y. 1970).

However, the range of action of these previously known compounds has some gaps and their microbicidal activity is not always satisfactory in certain areas of indication.

New 4-halogeno-5-nitrothiazole derivatives of the formula (I)

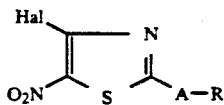

(I)

in which
Hal represents halogen,
A represents O, S, SO, $SO_2$ or N—$R^1$, wherein
  $R^1$ represents hydrogen, alkyl, alkenyl, halogenoalkyl or cyanoalkyl, or represents cycloalkyl, aryl or aralkyl, in each case optionally substituted by one or more identical or different substituents, and
R represents hydrogen, alkyl, alkenyl or alkinyl, it being possible for the abovementioned radicals in each case to be optionally substituted by one or more identical or different substituents from the group comprising halogen, alkoxy, aryloxy, alkylmercapto, arylmercapto and cyano, or represents cycloalkyl which is optionally substituted by one or more identical or different alkyl substituents, it being possible for a ring to be fused on in addition to the alkyl substitution, or represents aralkyl which is optionally substituted in the aryl part by one or more identical or different substituents from the group comprising halogen, alkyl, halogenoalkyl, nitro, alkoxy, alkylmercapto and cyano, or represents aryl which is optionally substituted by one or more identical or different substituents from the group comprising halogen, alkyl, alkenyl, alkinyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or R and $R^1$, together with the nitrogen atom on which they stand, form a ring which can optionally be interrupted by one or more further identical or different hetero atoms and which can optionally be substituted by one or more identical or different substituents, with the exception that R is not hydrogen if A represents SO or $SO_2$, have been found.

It has furthermore been found that the 4-halogeno-5-nitrothiazole derivatives of the formula (I)

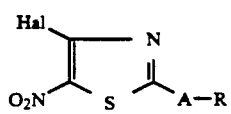

(I)

in which
Hal represents halogen,
A represents O, S, SO, $SO_2$ or N—$R^1$, wherein
  $R^1$ represents hydrogen, alkyl, alkenyl, halogenoalkyl or cyanoalkyl, or represents cycloalkyl, aryl or aralkyl, in each case optionally substituted by one or more identical or different substituents, and
represents hydrogen, alkyl, alkenyl or alkinyl, it being possible for the abovementioned radicals in each case to be optionally substituted by one or more identical or different substituents from the group comprising halogen, alkoxy, aryloxy, alkylmercapto, arylmercapto and cyano, or represents cycloalkyl which is optionally substituted by one or more identical or different alkyl substituents, it being possible for a ring to be fused on in addition to the alkyl substitution, or represents aralkyl which is optionally substituted in the aryl part by one or more identical or different substituents from the group comprising halogen, alkyl, halogenoalkyl, nitro, alkoxy, alkylmercapto and cyano, or represents aryl which is optionally substituted by one or more identical or different substituents from the group comprising halogen, alkyl, alkenyl, alkinyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or R and $R^1$, together with the nitrogen atom on which they stand, form a ring which can optionally be interrupted by one or more further identical or different hetero atoms and which can optionally be substituted by one or more identical or different substituents, with the exception that R is not hydrogen if A represents SO or $SO_2$, are obtained by a process in which
  a) in the case where A represents O, S, $SO_2$ or $NR^1$, 2,4-dihalogeno-5-nitrothiazoles of the formula (II)

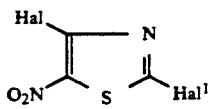

in which

Hal and Hal¹ denote identical or different halogen atoms, are reacted with nucleophiles of the formula (III)

in which

R has the abovementioned meaning and

A' represents O, S, $SO_2$ or $NR^1$, wherein $R^1$ has the abovementioned meaning, or metal salts thereof, if appropriate in the presence of acid-binding agents and in the presence of diluents, b) in the case where A—R represents

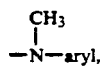

2,4-dihalogeno-5-nitrothiazoles of the formula (II) are reacted with N,N-dimethylarylamines of the formula (IV)

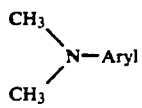

in which aryl has the meaning given for aryl under R, in the presence of diluents, c) in the case where A represents $SO_2$ or SO, 4-halogeno-5-nitrothiazolyl sulphides of the formula (V)

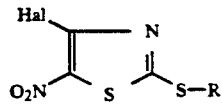

in which Hal and R have the abovementioned meanings,

α) are reacted with at least 2 mols of an oxidizing agent in the presence of a diluent which is inert under the reaction conditions, or β) are reacted with about 1 mol of an oxidizing agent in the presence of a diluent which is inert under the reaction conditions.

Finally, it has been found that the new 4-halogeno-5-nitrothiazole derivatives of the formula (I) have a potent action against pests, above all against fungi in the plant kingdom and against microbes in industrial materials.

Suprisingly, the 4-halogeno-5-nitrothiazole derivatives of the formula (I) according to the invention amongst other things exhibit a considerably more potent fungicidal activity in plant protection than, for example, the commercial products Captan (N-trichloromethylthio-tetrahydrophthalimide), Euparen (N,N-dimethyl-N'-phenyl-N'-(fluorodichloromethylthio)-sulphamide or Curzate [2-cyano-N-(ethylaminocarbonyl)-2-methoximino)-acetamide], which are known from the prior art and are closely related compounds from the point of view of their action. In addition, they have a better microbicidal action in materials protection than the known 4-benaimidazol-2-yl-thiazole.

In the context of the present invention, the substituents have the meanings given, and in general some substituents are listed below.

Halogen can, wherever this is not indicated otherwise, denote fluorine, chlorine, bromine and iodine.

Alkyl here in general in R represents a straight-chain or branched hydrocarbon radical having 1 to 12 carbon atoms. Examples which may be mentioned are methyl, ethyl, propyl, isopropyl, butyl, isobutyl, t-butyl, pentyl, isopentyl, hexyl, isohexyl, heptyl, isoheptyl, octyl and isooctyl.

Alkenyl in general in R represents a straight-chain or branched hydrocarbon radical having 3 to 12 carbon atoms and one or more, preferably one or two, double bonds. Examples which may be mentioned are allyl, propenyl, isopropenyl, butenyl, isobutenyl, pentenyl, isopentenyl, hexyl, isohexyl, heptenyl, isoheptenyl, octenyl and isooctenyl.

Cycloalkyl in general in R represents a cyclic hydrocarbon radical having 3 to 8 carbon atoms. The cyclopropyl, cyclopentyl or cyclohexyl ring is preferred. Examples which may be mentioned are cyclopropyl, cyclopentyl, cyclohexyl, cycloheptyl and cyclooctyl.

Halogenoalkyl in general represents straight-chain or branched lower alkyl having 1 to 8 carbon atoms and one or more halogen atoms. Examples which may be mentioned are: fluoromethyl, chloromethyl, bromomethyl, fluoroethyl, chloroethyl, bromoethyl, fluoropropyl, chloropropyl, bromopropyl, fluorobutyl, chlorobutyl, bromobutyl, fluoroisopropyl, chloroisopropyl, bromoisopropyl, difluoromethyl, trifluoromethyl, dichloromethyl, trichloromethyl, difluoroethyl, dichloroethyl, trifluoroethyl, tetrafluoroethyl, pentafluoroethyl, trichloroethyl and trifluoropropyl. Trifluoromethyl, difluoromethyl, fluoromethyl, chloromethyl and trifluoroethyl are especially preferred. Halogenoalkenyl in general represents straight-chain or branched alkenyl having up to 8 carbon atoms, one or more identical or different halogen atoms and one or more double bonds. Radicals with one double bond are preferred. Examples which may be mentioned are 2,2-dichlorovinyl and 1,2,2-trichlorovinyl.

Aryl can represent an aromatic hydrocarbon radical having 6 to 12 carbon atoms. Examples which may be mentioned are phenyl and naphthyl. Phenyl and naphthyl are preferred.

Aralkyl can represent a radical having 7 to 16 carbon atoms, it being possible for a straight-chain or branched alkyl radical having 1 to 4 carbon atoms to be substituted by an aromatic radical having 6 to 12 carbon atoms. Examples which may be mentioned are benzyl, phenethyl and phenylpropyl. Benzyl and phenethyl are preferred.

The aryl and aralkyl radicals can optionally be substituted by one or more identical or different substituents.

Alkoxyalkyl and alkylmercaptoalkyl in general represent a straight-chain or branched hydrocarbon radical which has 1 to 4 carbon atoms per alkyl part and is bonded via oxygen or sulphur. Examples which may be mentioned are methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl, butoxymethyl, butoxyethyl, butoxypropyl and butoxybutyl.

Furthermore methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl and butylthiobutyl.

Formula (I) provides a general definition of the 4-halogeno-5-nitrothiazole derivatives according to the invention. Preferred compounds of the formula (I) are those in which Hal represents fluorine, chlorine, bromine or iodine,
A represents O, S, SO, $SO_2$ or $NR^1$, wherein
  $R^1$ represents hydrogen, alkyl having 1 to 4 carbon atoms, alkenyl having 3 to 5 carbon atoms or halogenoalkyl having 1 to 3 carbon atoms and 1 to 5 identical or different halogen atoms, or represents cyanoalkyl having 1 or 2 carbon atoms in the alkyl part, or represents cycloalkyl having 3 to 6 carbon atoms, or represents phenyl or phenylalkyl having 1 to 3 carbon atoms in the alkyl part and in each case optionally substituted by one to three identical or different substituents from the group comprising alkyl having 1 to 4 carbon atoms, fluorine, chlorine, bromine and alkoxy having 1 to 4 carbon atoms and
R represents hydrogen, alkyl having 1 to 12 carbon atoms, alkenyl having 3 to 12 carbon atoms, alkinyl having 4 to 12 carbon atoms or halogenoalkyl, halogenoalkenyl or halogenoalkinyl having in each case up to 8 carbon atoms and 1 to 10 identical or different halogen atoms, or represents alkoxyalkyl, alkylmercaptoalkyl or cyanoalkyl having 1 to 4 carbon atoms per alkyl part, or represents phenyloxyalkyl or phenylmercaptoalkyl having 1 to 4 carbon atoms in the alkyl part, it being possible for the phenyl radicals to be optionally substituted by one to three identical or different substituents from the group comprising fluorine, chlorine, bromine and alkyl having 1 to 4 carbon atoms, or represents cycloalkyl having 3 to 8 carbon atoms and optionally substituted by one to three identical or different alkyl substituents having 1 to 4 carbon atoms, it being possible for the cycloalkyl ring additionally to contain a fused-on ring, or represents phenylalkyl having 1 to 4 carbon atoms in the alkyl part and optionally substituted by one to five identical or different substituents from the group comprising halogen, alkyl having 1 to 4 carbon atoms, halogenoalkyl having 1 to 4 carbon atoms and 1 to 8 identical or different halogen atoms, nitro, cyano, alkoxy having 1 to 4 carbon atoms and alkylmercapto having 1 to 4 carbon atoms, the alkyl part of the phenylalkyl optionally containing, as a substituent, a further phenyl radical which can optionally be substituted as described above, or represents phenyl which is optionally substituted by one to five identical or different substituents from the group comprising halogen, nitro, alkyl having 1 to 12 carbon atoms, alkoxy, alkylmercapto, carbalkoxy, alkylsulphonylamino, alkylsulphonyl, sulphamoyl, N-alkylsulphamoyl, N,N-dialkylsulphamoyl, dialkylamino, carbamoyl, N-alkylcarbamoyl or N,N-dialkylcarbamoyl having in each case 1 to 4 carbon atoms per alkyl radical, halogenoalkyl, halogenoalkoxy or halogenoalkylmercapto having in each case 1 to 4 carbon atoms and 1 to 8 identical or different halogen atoms per radical listed, phenyl, phenoxy, phenylmercapto, acyloxy having 1 to 3 carbon atoms, acyl having 1 to 3 carbon atoms, phenylalkyloxy having 1 to 3 carbon atoms in the alkyl part, phenylalkylmercapto having 1 to 3 carbon atoms, acylamino having 1 to 3 carbon atoms, acylalkylamino having 1 to 3 carbon atoms per acyl and alkyl radical, cycloalkyl having 4 to 6 carbon atoms and cyano, or represents naphthyl, or R and $R^1$, together with the nitrogen atom on which they stand, form a ring having 5 to 7 ring members, which can optionally contain one or two further nitrogen and/or oxygen atoms and can optionally be substituted by one to three alkyl radicals having 1 to 4 carbon atoms, with the exception that R is not hydrogen if A represents SO or $SO_2$.

Particularly preferred compounds of the formula (I) are those in which

Hal represents chlorine, bromine or iodine,
A represents O, S, SO, $SO_2$ or $NR^1$, wherein
  $R^1$ represents hydrogen, alkyl having 1 to 4 carbon atoms or alkenyl having 3 or 4 carbon atoms, or represents phenyl, benzyl or 2-phenyl-2-methylethyl which is optionally substituted by one to three alkyl substituents having 1 to 3 carbon atoms, and
R represents hydrogen, alkyl having 1 to 8 carbon atoms, alkenyl having 3 to 8 carbon atoms, alkinyl having 4 to 8 carbon atoms, cyanoalkyl having 1 to 3 carbon atoms in the alkyl part, cycloalkyl having 3 to 6 carbon atoms, or represents phenyl, benzyl, phenethyl or naphthyl, optionally substituted by one to five identical or different substituents from the group comprising alkyl having 1 to 12 carbon atoms, alkenyl having up to 3 carbon atoms, fluorine, chlorine, bromine, iodine, trifluoromethyl, nitro, alkoxy having 1 to 4 carbon atoms, alkylmercapto having 1 to 4 carbon atoms, dialkylamino having 1 or 2 carbon atoms per alkyl radical, carbalkoxy having 1 to 2 carbon atoms, trifluoromethoxy, trifluoromethylmercapto, alkylsulphonylamino having 1 or 2 carbon atoms, alkylsulphonyl having 1 or 2 carbon atoms, phenyl, phenoxy, phenylmercapto, acetoxy, acetyl, carbamoyl, sulphamoyl, N,N-dialkylsulphamoyl having 1 or 2 carbon atoms per alkyl radical, benzyloxy, benzylmercapto, formylamino, formylmethylamino, acetylamino, cyclopentyl, cyclohexyl and cyano, or R and $R^1$, together with the nitrogen atom on which they stand, represent pyrrolidine, piperidine, hexamethyleneimine, morpholine, N-alkylpiperazine ($C_1$-$C_2$), pyrrole, pyrazole, imidazole or 1,2,4-triazole, optionally substituted by one or two alkyl substituents having 1 or 2 carbon atoms, with the exception that R is not hydrogen if A represents SO or $SO_2$.

Compounds of the formula (I) which are to be especially singled out are those in which Hal represents halogen and
A—R represents OR, wherein
  R represents alkyl, alkenyl or alkinyl, or represents cycloalkyl which is optionally substituted by one or more identical or different alkyl substituents, it being possible for a ring to be fused on in addition to the alkyl substitution, or represents aralkyl which is optionally substituted in the aryl part by one or more identical or different substituents from the group comprising halogen, alkyl, halogenoalkyl, nitro, alkoxy, alkylmercapto and cyano, or represents aryl which is optionally substituted by one or more identical or different substituents from the group comprising halogen, alkyl, alkenyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or A—R represents SR, wherein represents alkyl, alkenyl or alkinyl, or represents cycloalkyl which is optionally substituted by one or more identical or different alkyl substituents, it being possible for a ring to be fused on in addition to the alkyl substitution, or represents aralkyl which is optionally substituted in the aryl part by one or more identical or different substituents from the group comprising halogen, alkyl, halogenoalkyl, nitro, alkoxy, alkylmercapto and cyano, or represents aryl which is optionally substituted by one or more identical or different substituents from the group comprising halogen, alkyl, alkenyl, halogenoalkyl, nitro, alkoxy, alkylmercapto, dialkylamino, carbalkoxy, carbamoyl, N-alkylcarbamoyl, N,N-dialkylcarbamoyl, halogenoalkoxy, halogenoalkylmercapto, alkylsulphonylamino, alkylsulphonyl, aryl, aryloxy, arylmercapto, acyloxy, acyl, sulphamoyl, N-alkysulphamoyl, N,N-dialkylsulphamoyl, aralkoxy, aralkylmercapto, acylamino, acylalkylamino, cycloalkyl and cyano, or A—R represents $SO_nR$, wherein n represents 1 or 2 and R represents aryl which is optionally substituted by one or more identical or different substituents from the group comprising halogen, alkyl, alkenyl, halogenoalkyl, nitro, alkoxy, alkylmercapto, dialkylamino, carbalkoxy, carbamoyl, N-alkylcarbamoyl, N,N-dialkylcarbamoyl, halogenoalkoxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or A—R represents —NH—R, wherein represents alkenyl, alkinyl, or represents cycloalkyl which is optionally substituted by one or more identical or different alkyl substituents, it being possible for a ring to be fused on in addition to the alkyl substitution, or represents aralkyl which is optionally substituted in the aryl part by one or more identical or different substituents from the group comprising halogen, alkyl, halogenoalkyl, nitro, alkoxy, alkylmercapto and cyano, or represents aryl which is optionally substituted by one or more identical or different substituents from the group comprising halogen, alkyl, halogenoalkyl, nitro, dialkylamino, carbalkoxy, carbamoyl, N-alkylcarbamoyl, N,N-dialkylcarbamoyl, halogenomethyloxy, halogenomethylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or A—R represents

wherein

R[1] represents alkyl, alkenyl, halogenoalkyl or cyanoalkyl or represents cycloalkyl, aryl or aralkyl, in each case optionally substituted by one or more identical or different substituents, and R represents alkyl, alkenyl or alkinyl, it being possible for the abovementioned radicals in each case to be optionally substituted by one or more identical or different substituents from the group comprising halogen, alkoxy, aryloxy, alkylmercapto, arylmercapto and cyano, or represents cycloalkyl which is optionally substituted by one or more identical or different alkyl substituents, it being possible for a ring to be fused on in addition to the alkyl substitution, or represents aralkyl which is optionally substituted in the aryl part by one or more identical or different substituents from the group comprising halogen, alkyl, halogenoalkyl, nitro, alkoxy, alkylmercapto and cyano, or represents aryl which is optionally substituted by one or more identical or different substituents from the group comprising halogen, alkyl, alkenyl, halogenoalkyl, nitro, dialkylamino, carbalkoxy, carbamoyl, N-alkylcarbamoyl, N,N-dialkylcarbamoyl, halogenomethyloxy, halogenomethylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or R and R[1], together with the nitrogen atom on which they stand, form a ring which can optionally be interrupted by one or more further identical or different hetero atoms and can optionally be substituted by one or more identical or different substituents.

The number of carbon atoms, the substituents and the number of substituents correspond to the data in the preferred definition.

If 2,4-dichloro-5-nitrothiazole and aniline are used as starting substances in process (a) according to the invention, the course of the reaction can be represented by the following equation:

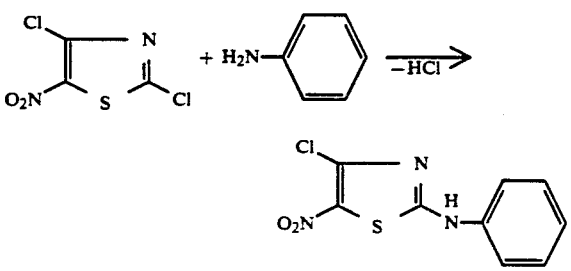

If 2,4-dichloro-5-nitrothiazole and N,N-dimethylaniline are used as starting substances, the course of process (b)

according to the invention can be represented by the following equation:

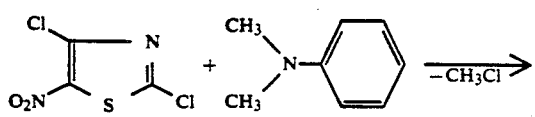
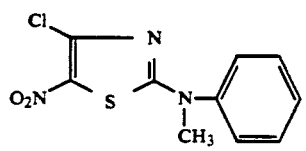

If 4-chloro-2-(4-methylphenylmercapto)-5-nitrothiazole and 2 mols of 3-chloroperoxybenzoic acid are used as starting substances, the course of process (c), variant α, according to the invention can be represented by the following equation:

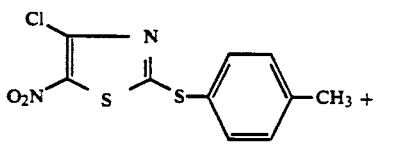
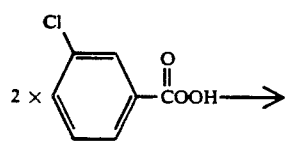
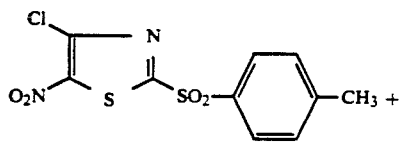
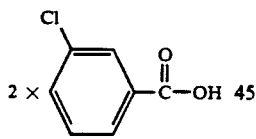

If 4-chloro-2-(4-methylphenylmercapto)-5-nitrothiazole is used as the starting substance and 1 mol of 3-chloroperoxybenzoic acid is used as the oxidizing agent, the course of process (c), variant β, according to the invention can be represented by the following equation:

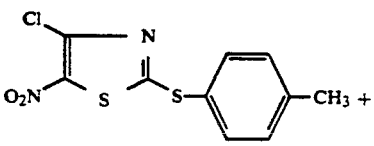
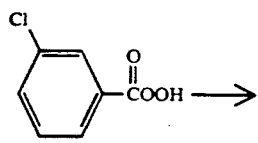

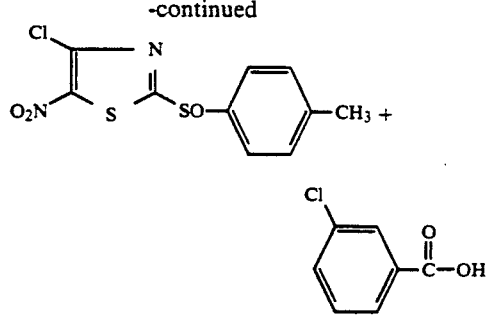
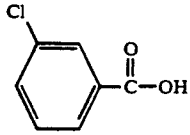

The 2,4-dihalogeno-5-nitrothiazoles of the formula (II) required as starting substances in process (a) according to the invention are known in some cases, for example for compounds of the formula (II) in which
Hal=Hal$^1$=bromine: Chem. Abstr. 61: 3087 f and for
Hal=Hal$^1$=chlorine, compare DE-OS (German Published Specification) 3,518,520.

The two compounds mentioned are producible, for example, by nitration of the corresponding 2,4-dihalogenothiazoles.

Compounds of the formula (II A)

(II A)

in which
Hal' and Hal$^{1'}$ independently of one another represents chlorine, iodine or fluorine, with the proviso that the two Hals may not simultaneously be chlorine,
are new and likewise form part of the invention. At appropriate concentrations, these substances also display a microbicidal action.

Thus, compounds of the formula (II A) in which
Hal'=Hal$^{1'}$=iodine or
Hal'=chlorine and Hal$^{1'}$=iodine or
Hal'=iodine and Hal$^{1'}$=chlorine or
Hal'=chlorine and Hal$^{1'}$=fluorine
for example, are new. The iodine compounds are thus obtained by reaction of 2,4-dichloro-5-nitrothiazole with metal iodides, in particular sodium iodide, in lower aliphatic ketones, in particular acetone, as the solvent in accordance with the following equations:

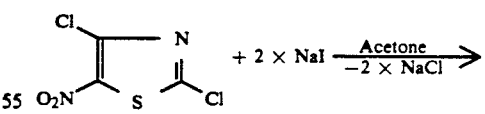
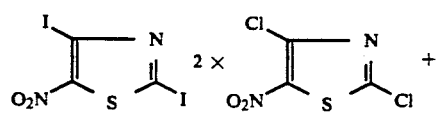
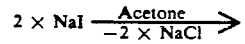
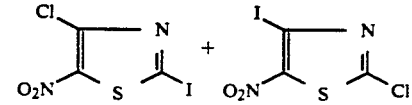

The two isomeric chloro-iodo-nitrothiazoles are formed side by side and can be separated from one another by fractional crystallization and/or by chromatographic methods. The reaction temperature is in general between 0° C. and 130° C., preferably between 10° C. and 90° C.

Compounds of the formula (II A) in which at least one of the halogens is fluorine, for example Hal$^{1'}$=fluorine and Hal$'$=chlorine, that is to say 4-chloro-2-fluoro-5-nitrothiazole, can be prepared by reacting 2,4-dichloro-5-nitrothiazole with metal fluorides, in particular sodium fluoride or potassium fluoride, in lower aliphatic nitriles, in particular in acetonitrile or propionitrile, as the solvent in the presence of catalytic amounts of crown ethers, in particular of [18] crown-6. The reaction temperature is 0° C. to 50° C., preferably 10° C. to 30° C. 2-15 mols of metal fluoride, preferably 3-12 mols of metal fluoride, are used per mol of 2,4-dichloro-5-nitrothiazole.

The nucleophiles of the formula (III) furthermore required as starting substances in process (a) according to the invention are known in principle. If specific compounds have not yet been described, they can be prepared by known processes.

Possible solvents in carrying out process (a) according to the invention are: aliphatic nitriles, in particular acetonitrile, open-chain or cyclic dialkylamides of aliphatic carboxylic acids, such as dimethylformamide and N,N-dimethylacetamide, and furthermore N-methyl-2-pyrrolidinone, N-methylcaprolactam, tetramethylurea, N,N'-dimethyl-1,3-imidazolin-2-one, hexamethylphosphoric acid trisamide, dimethyl sulphoxide, dimethyl sulphone, tetramethylene sulphone (=sulpholane), tetrahydrofuran, dioxane and lower aliphatic alcohols, in particular in connection with their associated metal salt, in particular alkali metal salt.

Cyclic ethers, such as dioxane, and above all the aprotic polar solvents, such as dimethylformamide and N-methyl-2-pyrrolidinone, as well as acetonitrile are preferably used.

The choice of solvents also depends on the nature of the nucleophile of the formula (III). If the nucleophile or its metal salt, preferably alkali metal salt, is used in the form of an aqueous solution (such as, for example, in sodium hydroxide solution or methylamine), a mixed system of water and one of the solvents mentioned can also be used.

Weakly basic amines, such as, for example, pyrrole, pyrazole, diphenylamine or aniline derivatives which are substituted by negative substituents, such as, for example, nitro or trifluoromethyl, can be reacted particularly advantageously using aprotic polar solvents, such as dimethylformamide or N-methyl-2-pyrrolidinone, whereas strong bases, such as, for example, aliphatic amines, such as, for example, diethylamine or morpholine, also react rapidly in dioxane or acetonitrile. The reaction temperature can be varied within wide ranges in process (a) according to the invention. The reaction is in general carried out between −50° C. and +150° C., preferably at −20° C. to 100° C.

Strong nucleophiles in general already react very rapidly in the desired sense at the lower limit of the temperature range mentioned, whereas weak nucleophiles require higher temperatures and longer reaction times.

The reactions are as a rule carried out under normal pressure, but the reaction can also be carried out in closed vessels in which a correspondingly higher pressure is then established according to the nature of the solvent and the temperature.

To bind the hydrogen halide liberated in accordance with the equation in process (a) according to the invention an acid-binding agent is in general necessary. For this there can be used, for example: alkali metal hydroxides, carbonates or bicarbonates.

Instead of using the acid-binding agent, metal salts, preferably alkali metal salts, of the nucleophile of the formula (III) in question can also be reacted directly. The salts can either be used as such or produced in situ, for example by addition of alkali metal hydrides, preferably sodium hydride.

If the nucleophiles to be employed are strongly basic amines, such as, for example, diethylamine, a corresponding excess of the nucleophile can serve as the acidbinding agent. More weakly basic amines, such as anilines, which are reacted in aprotic, strongly polar solvents, such as dimethylformamide or N-methyl-2-pyrrolidinone, give the desired compounds of the formula (I) in good yields without the addition of an acid-binding agent and without using an excess of the nucleophile.

Very weak nucleophiles of the formula (III), for example anilines substituted by two or more negative substituents, especially those which have these negative substituents in the ortho-positions relative to the amino group, are advantageously reacted in ethers, in particular in cyclic ethers, such as, for example, tetrahydrofuran or dioxane, with the addition of metal hydrides, preferably sodium hydride, for the purpose of salt formation in situ.

The reaction partners are in general reacted with one another in the stoichiometrically equimolar ratio, and in the case of strongly basic amines, which can simultaneously function as the acid-binding agent, in twice the molar ratio.

Since the 2,4-dihalogeno-5-nitrothiazoles of the formula (II) carry a second—although of a reactivity which is a significant step lower—halogen atom in the 4-position, it is generally advantageous not to employ an excess of nucleophile of the formula (III). In certain cases, however, it may be advantageous to employ an excess of 2,4-dihalogeno-5-nitrothiazole of the formula (II), which can in general be 20 mol percent up to 100 mol percent. In the case of weak nucleophiles of the formula (III) which react only relatively slowly with the considerably more reactive halogen in the 2-position of the thiazole ring, on the other hand, an excess of the nucleophile of the formula (III), which can be up to 100 mol percent, can be employed.

In carrying out process (a) according to the invention, the 2,4-dihalogeno-5-nitrothiazole of the formula (II) is preferably initially introduced into one of the solvents mentioned and the acid-binding agent is then added, if appropriate. The nucleophile of the formula (III) is then slowly added in small portions, for example by dropwise addition of a solution or in a diluent, at room temperature or below, particularly preferably down to −15° C. Local excesses of nucleophile of the formula (III) during reaction with the 2,4-dihalogeno-5-nitrothiazole of the formula (II) are to the greatest extent avoided by this measure of slow addition, and formation of disubstitution products which are undersirable here is thus virtually excluded.

If the desired final reaction temperature is to be above room temperature, the mixture is subsequently heated.

The reaction products are isolated by customary methods. In the simplest case, the reaction mixture is stirred into excess ice-water, for example 5 to 10 times the amount by volume of the solvent employed, if appropriate after partial or complete removal of the solvent by distillation in vacuo below the reaction temperature, and the product is filtered off, washed with water and dried. If an excess of 2,4-dihalogeno-5-nitrothiazole has been used, this can be dissolved out of the well-dried crude product by stirring at room temperature with a solvent which dissolves virtually only the 2,4-dihalogeno-5-nitrothiazole of the formula (II), and if appropriate can be re-used for subsequent batches. In the case of 2,4-dichloro-5-nitrothiazole, petroleum ether, for example, is particularly suitable. If the reaction product which still contains excess 2,4-dihalogeno-5-nitrothiazole of the formula (II) is itself readily soluble in petroleum ether at room temperature, the 2,4-dihalogeno-5-nitrothiazole of the formula (II) is subjected, for example, to fractional sublimation or distillation from the usually significantly less volatile reaction product in vacuo under about 0.1 mbar. In the case of 2,4-dichloro-5-nitrothiazole this is possible, for example, at a temperature of about 70° C. under 0.1 mbar. Further purification of the reaction products can be effected, for example, by recrystallization or by a chromatographic route.

If a reaction product is obtained as an oil when the mixture is stirred in excess ice-water, it is isolated by extraction several times by shaking with one of the usual organic water-immiscible solvents, such as, for example, methylene chloride, by separating off the organic phase, washing it with water if appropriate, for example in the case of dimethylformamide or N-methyl-2-pyrrolidinone as the reaction medium, drying it and concentrating it in vacuo.

The N,N-dimethylarylamines of the formula (IV) required as starting substances in process (b) according to the invention are known in principle. If specific compounds have not yet been described, they can be prepared by known methods. In formula (IV), aryl has the same meaning as aryl in the definition of R in formula (I).

Possible solvents in carrying out process (b) according to the invention are aliphatic or aromatic nitriles, for example acetonitrile, propionitrile or benzonitrile, in particular acetonitrile, and ethers, in particular cyclic ethers, such as dioxane and tetrahydrofuran, in particular dioxane.

The reaction temperature can be varied within wide ranges in process (b) according to the invention. The reaction is in general carried out between 50° C. and 200° C., preferably at 60° C. to 150° C.

The reactions are as a rule carried out under normal pressure, but the reaction can also be carried out in closed vessels in which a correspondingly higher pressure is then established according to the nature of the solvent and the temperature.

The reaction partners are preferably reacted with one another in stoichiometrically equimolar ratio.

In carrying out process (b) according to the invention, the 2,4-dihalogeno-5-nitrothiazole of the formula (II) is preferably dissolved in one of the solvents mentioned, preferably the approximately equimolar amount of N,N-dimethylarylamine is added and the mixture is heated, preferably under reflux, until the reaction has virtually ended. The solvent is then distilled off, preferably in vacuo, and the residue is purified, if necessary, for example by recrystallization.

Formula (V) provides a definition of the 4-halogeno-5-nitrothiazolyl sulphides according to the invention required as starting substances in process (c) according to the invention. In this formula, Hal and R preferably represent those radicals which have already been mentioned in connection with the description of the substances of the formula (I) according to the invention.

All the customary reagents which can be used for such purposes can be employed as oxidizing agents in process (c) according to the invention. Aliphatic or aromatic percarboxylic acids, such as, for example, peracetic acid, perpropionic acid and 3-chloroperbenzoic acid, are preferred. 3-Chloroperbenzoic acid is particularly preferred.

All the customary inert organic solvents can be used as solvents in process (c) according to the invention. Preferred possible solvents are methylene chloride, chloroform and carbon tetrachloride.

The reaction temperatures can be varied within a certain range in process (c) according to the invention. The reaction is in general carried out at temperatures between 0° C. and 100° C., preferably between 20° C. and 80° C.

In carrying out process (c), variant α, according to the invention, the 4-halogeno-5-nitrothiazolyl sulphide of the formula (V) is in general dissolved in one of the solvents mentioned and at least 2 mols of an oxidizing agent, preferably one of the percarboxylic acids mentioned, preferably up to 5 mols of oxidizing agent per mol of the compound of the formula (V), are added and the mixture is stirred, for example while monitoring by thin layer chromatography, until the desired reaction has ended. Reflux conditions are preferably used here in order to accelerate the reaction.

In carrying out process (c), variant β, according to the invention, the 4-halogeno-5-nitrothiazolyl sulphide of the formula (V) is dissolved in one of the solvents mentioned and small portions of oxidizing agent, preferably percarboxylic acid, are added to avoid sulphone formation which is undesirable here, preferably in the lower range of the reaction temperature mentioned, for example at room temperature, the reaction being monitored by thin layer chromatography. The total amount of oxidizing agent, for example percarboxylic acid, is preferably in the range from 1 to 1.5 mols per mol of compound of the formula (V). Since the reaction of course proceeds relatively slowly at low temperatures, for example at room temperature, the reaction can be stopped with the aid of thin layer chromatography, even when more than 1 mol of percarboxylic acid is used per mol of compound of the formula (V), before noticeable amounts of undesirable sulphone are formed.

The sulphones or sulphoxides are isolated in the pure form in the customary manner. The solvent is stripped off in vacuo, the residue is stirred with excess aqueous sodium bicarbonate solution at room temperature, in order to remove, for example, the (per)carboxylic acids, the mixture is filtered and the residue is washed with water, dried and if appropriate recrystallized, for example from hydrocarbons, such as cyclohexane.

The active compounds of the formula (I) according to the invention have a potent action against pests and can be used in practice for combating undesirable harmful organisms. The active compounds are suitable for use as plant protection agents, above all as fungicides and in addition for protecting industrial materials against microbes, such as, for example, fungi, bacteria and slime organisms.

Fungicidal agents in plant protection are employed for combating Plasmodiophoromycetes, Oomycetes, Chytridiomycetes, Zygomycetes, Ascomycetes, Basidiomycetes and Deuteromycetes. Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. *oryzae*; Pseudomonas species, such as, for example, *Pseudomonas syringae* pv. *lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Utilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating fruit, vegetable and cereal diseases, such as, for example, against the apple scab causative organism (*Venturia inaequalis*), the brown rot of tomato causative organism (*Phytophthora infestans*), vine disease causative organisms (*Plasmopara viticola*) or cereal disease causative organisms, such as, for example, *Leptosphaeria nodorum*, *Fasarium nivale* and *Pyrenophora teres*. The action against the rice spot disease causative organisms (*Pyricularia oryzae*) and the broad in vitro action may also be mentioned. When used in appropriate concentrations, many of the compounds according to the invention also have a bactericidal action.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals; such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

Due to their broad range of action, the active compounds of the formula (I) according to the invention are furthermore suitable for the protection of industrial materials.

Since industrial materials can be infested and damaged by very many and a wide variety of microbe species, a broad range of action which also makes possible a wide range of uses is an essential property of advanced material protection compounds.

According to the invention, industrial materials are nonliving materials which have been prepared for use in industry. For example, industrial materials which are to be protected by active compounds according to the invention against change or destruction by microbes are adhesives, glues, paper and board, textiles, leather, wood, paints and plastic articles, cooling lubricants and other materials which can be infested or destroyed by microorganisms. Within the context of materials to be protected, parts of production plants, for example coolingwater circuits, which can be impaired by multiplication of microorganisms, may also be mentioned. In the context of the present invention, industrial materials which may be mentioned are preferably adhesives, glues, papers and boards, leather, wood, paints, cooling lubricants and cooling circuits.

Examples of microorganisms which can cause degradation or change in industrial materials are bacteria, fungi, yeasts, algae and slime organisms. The active compounds according to the invention preferably act against fungi, in particular mold fungi, fungi which discolor and destroy wood (Basidiomycetes), and against slime organisms and algae.

Examples of microorganisms which may be mentioned are those of the following genera:
Alternaria, such as *Alternaria tenuis*,
Aspergillus, such as *Aspergillus niger*,
Chaetomium, such as *Chaetomium globosum*,
Coniophora, such as *Coniophora puteana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on the area of application, an active compound according to the invention can be converted into the customary formulations, such as solutions, emulsions, suspensions, powders, pastes and granules.

These can be prepared in a known manner, for example by mixing the active compounds with an extender which comprises liquid solvent and/or solid carriers, if appropriate using surface-active agents, such as emulsifiers and/or dispersants, it being possible, if appropriate, to use organic solvents such as alcohols as auxiliaries in the case of the use of water as extender.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as petroleum fractions, and halogenated hydrocarbons, such as 1,2-dichloroethane.

Microbicidal agents generally contain the active compounds in an amount of from 1 to 95%, preferably 10 to 75%.

The use concentrations of the active compounds according to the invention depend on the species and occurrence of the microorganisms to be controlled, and on the composition of the material to be protected. The optimum amounts used can be determined by series of tests. In general, the use concentrations are in the range from 0.001 to 5% by weight, preferably 0.05 to 1.0% by weight, relative to the material to be protected.

The active compounds according to the invention can also be in the form of a mixture with other known active compounds. The following active compounds may be mentioned as examples: benzyl alcohol mono(poly)hemiformal and other formaldehyde-eliminating compounds, benzimidazolyl methylcarbamates, tetramethylthiuram disulphide, zinc salts of dialkyl dithiocarbamates, 2,5,5,6-tetrachloroisophthalonitrile, thiazolylbenzimidazole, mercaptobenzothiazole, 2-thiocyanatomethylthiobenzothiazole, methylene bisthiocyanate, phenol derivatives, such as 2-phenylphenol, (2,2'-dihydroxy-5,5'-dichloro)-diphenylmethane and 3-methyl-4-chloro-phenol, and organotin compounds.

PREPARATION EXAMPLES

EXAMPLE 1

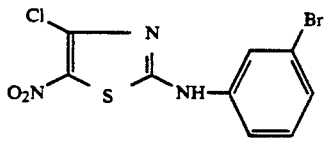

(Compound No. 51)

A solution of 8.6 g (0.05 mol) of 3-bromoaniline in 100 ml of dimethylformamide is added dropwise to a solution of 12.0 g (0.06 mol) of 2,4-dichloro-5-nitrothiazole in 100 ml of dimethylformamide at 0° C. to 5° C. in the course of about 2 hours and the mixture is subsequently stirred at the same temperature for a further 4 hours. It is then stirred into 1,000 ml of ice-water and the precipitate is filtered off, washed with water and dried. To remove excess 2,4-dichloro-5-nitrothiazole, the product is stirred in 80 ml of petroleum ether at room temperature, filtered off, washed with petroleum ether and dried. 16.0 g (95.7% of theory) of 2-(3bromophenylamino)-4-chloro-5-nitrothiazole of melting point 191° C. to 192° C. (decomposition) are thus obtained.

EXAMPLE 2

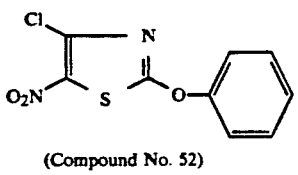

(Compound No. 52)

42 g (0.036 mol) of anhydrous potassium carbonate are added to a solution of 72.0 g (0.36 mol) of 2,4-dichloro-5-nitrothiazole in 300 ml of acetonitrile. A solution of 28.2 g (0.3 mol) of phenol in 300 ml of acetonitrile is then added dropwise at 15° C. to 20° C. in the course of about 1.5 hours and the mixture is subsequently stirred at the same temperature for a further 0.5 hour. It is then heated at the reflux temperature for 15 minutes, cooled to room temperature and then stirred into 3 liters of ice-water and the precipitate is filtered off, washed with water and dried. To remove excess 2,4-dichloro-5-nitrothiazole, the product is stirred in 500 ml of petroleum ether at about 20° C., filtered off, washed with petroleum ether and dried. 75.4 g (98.0% of theory) of 4-chloro-5-nitro-2-phenoxythiazole are thus obtained. Melting point 96° C. (from petroleum ether).

EXAMPLE 3

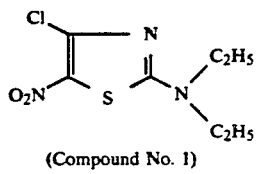

(Compound No. 1)

146 g (2 mols) of diethylamine are added dropwise to a solution of 199 g (1 mol) of 2,4-dichloro-5-nitrothiazole in 1 l of dioxane at 20° C. to 30° C. in the course of about 2 hours. After the mixture has been left to stand overnight at room temperature, it is stirred in 8 l of icewater and the precipitate is filtered off, washed with water and dried. 216 g (91.7% of theory) of 2-diethylamino-4-chloro-5-nitrothiazole of melting point 85° C. (from cyclohexane) are obtained.

EXAMPLE 4

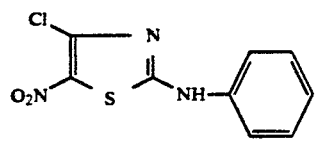

(Compound No. 5)

252 g (3.0 mols) of sodium bicarbonate are added to a solution of 360 g (1.8 mols) of 2,4-dichloro-5-nitrothiazole in 1.5 l of acetonitrile. A mixture of 139.5 g (1.5 mols) of aniline and 1,500 ml of acetonitrile is then added dropwise at −10° C. to −15° C. in the course of about 4.5 hours and the mixture is subsequently stirred at the same temperature for a further 4 hours. It is then stirred into 15 l of ice-water and the precipitate is filtered off, washed with water and dried. To remove excess 2,4-dichloro-5-nitrothiazole, the product is stirred into 2.4 l of petroleum ether at room temperature, filtered off, washed with petroleum ether and dried. 361.7 g (94.4% of theory) of 2-anilino-4-chloro-5-nitrothiazole of melting point 186° C. to 187° C. (decomposition) are obtained.

EXAMPLE 5

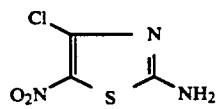

(Compound No. 3)

10.1 g (0.105 mol) of ammonium carbonate are added to a solution of 19.9 g (0.1 mol) of 2,4-dichloro-5-nitrothiazole in 200 ml of acetonitrile, while stirring, and stirring is continued at room temperature for two days. The mixture is then stirred into 1 l of ice-water and the precipitate is filtered off, washed with water and dried. To remove unreacted 2,4-dichloro-5-nitrothiazole, the product is stirred into about 100 ml of petroleum ether at room temperature, filtered off, washed with petroleum ether and dried. 12.2 g (68.0% of theory) of 2-amino-4-chloro-5-nitrothiazole of melting point 180° C. (decomposition) are obtained.

EXAMPLE 6

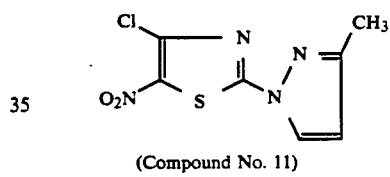

(Compound No. 11)

4.1 g (0.05 mol) of 3-methylpyrazole are added to a solution of 5.0 g (0.025 mol) of 2,4-dichloro-5-nitrothiazole in 50 ml of N-methyl-2-pyrrolidinone at room temperature. After the mixture has been left to stand at room temperature for four days, it is stirred into 500 ml of ice-water and the precipitate is filtered off, washed with water and dried. 5.8 g (94.9% of theory) of 4-chloro-2-(3-methyl-1-pyrazolyl)-5-nitrothiazole of melting point 153° C. are obtained.

EXAMPLE 7

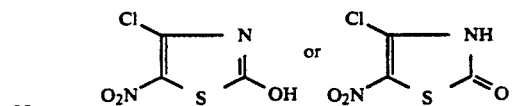

(Compound No. 17)

200 ml (0.2 mol) of an aqueous 1N sodium hydroxide solution are slowly added dropwise to a solution of 19.9 g (0.1 mol) of 2,4-dichloro-5-nitrothiazole in 200 ml of dioxane at 20° C. to 25° C. After stirring has been continued overnight at room temperature, the mixture is acidified with concentrated hydrochloric acid at 0° C. to 5° C. A total of 13.3 g (73.7% of theory) of 4-chloro-2-hydroxy-5-nitrothiazole and the desmotropic keto form formulated above, of melting point 136° C. (decomposition) are obtained by concentrating the resulting suspension to about one quarter of its volume at room temperature in vacuo.

EXAMPLE 8

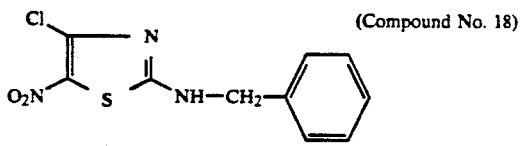

(Compound No. 18)

7.0 g (0.051 mol) of anhydrous potassium carbonate are added to a solution of 12.0 g (0.06 mol) of 2,4-dichloro-5-nitrothiazole in 50 ml of acetonitrile. A mixture of 5.35 g (0.05 mol) of benzylamine and 50 ml of acetonitrile is then added dropwise at 15° C. to 20° C. in the course of about half an hour and the mixture is subsequently stirred at room temperature for a further hour. It is then heated at the reflux temperature for 15 minutes, cooled to room temperature and stirred into about 500 ml of ice-water and the precipitate is filtered off, washed with water and dried. To remove excess 2,4-dichloro-5-nitrothiazole, the product is stirred into 80 ml of petroleum ether at room temperature, filtered off, washed with petroleum ether and dried. 12.9 g (95.7% of theory) of 2-benzylamino-4-chloro-5-nitrothiazole of melting point 195° C. to 196° C. (decomposition) are obtained.

EXAMPLE 9

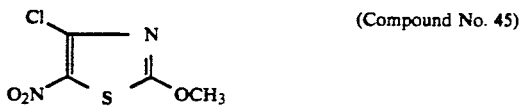

(Compound No. 45)

A mixture of 28.8 g (0.16 mol) of 30% strength sodium methanolate solution in methanol and 40 ml of methanol is added dropwise to a solution of 19.9 g (0.1 mol) of 2,4-dichloro-5-nitrothiazole in 100 ml of methanol at 0° C. to 5° C. in the course of about 1.5 hours and the mixture is subsequently stirred at room temperature for about a further hour. After the solvent has been stripped off at room temperature in vacuo, the residue is stirred with a mixture of 180 ml of 1N hydrochloric acid and 90 ml of water and the precipitate is filtered off, washed with water and dried. Yield: 9.9 g (50.9% of theory) of 4-chloro-2-methoxy-5-nitrothiazole of melting point 52° C. (from petroleum ether).

EXAMPLE 10

(Compound No. 67)

6.7 g (0.1 mol) of pyrrole are added to a solution of 10.0 g (0.05 mol) of 2,4-dichloro-5-nitrothiazole in 100 ml of N-methyl-2-pyrrolidinone at room temperature. The mixture is then heated at 70° C. for 5 hours and subsequently cooled to room temperature and stirred into 1 l of ice-water. The precipitate formed is filtered off, washed with water and dried. 8.25 g (72.0% of theory) of 4-chloro-5-nitro-2-(1-pyrrolyl)-thiazole of melting point 138° C. to 139° C. (yellow needles from toluene) are obtained.

EXAMPLE 11

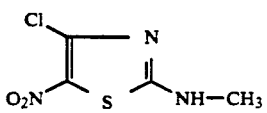

(Compound No. 18)

48.6 g (0.5 mol) of 31.9% strength aqueous methylamine solution are slowly added dropwise to a solution of 99.5 g (0.5 mol) of 2,4-dichloro-5-nitrothiazole in 1,000 ml of acetonitrile at −10° C., to 0° C., whereupon a precipitate separates out. After the mixture has been further stirred overnight at room temperature, it is stirred into 5 l of ice-water and the precipitate is filtered off, washed with water and dried. After stirring with about 500 ml of petroleum ether at room temperature, the product is filtered off, washed with petroleum ether and dried. 46.9 g (48.5% of theory, based on 2,4-dichloro-5-nitrothiazole, or 97% of theory, based on methylamine) of 4-chloro-2-methylamino-5-nitrothiazole of melting point 212° C. (decomposition) are obtained. The compound can be recrystallized from methanol and can be sublimed at 140° C./0.1 mbar.

EXAMPLE 12

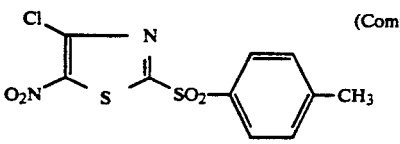

(Compound No. 66)

A solution, prepared by heating, of 8.9 g (0.05 mol) of

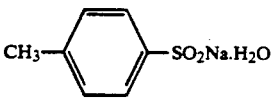

in 50 ml of dimethylformamide is slowly added dropwise to a solution of 19.9 g (0.1 mol) of 2,4-dichloro-5-nitrothiazole in 500 ml of dimethylformamide at 0° C. to 5° C., whereupon a precipitate separates out. After the mixture has been subsequently stirred at 0° C. to 5° C. for six hours, it is stirred into 5 l of ice-water and the precipitate is filtered off, washed with water and dried. 9.5 g (59.7% of theory) of 4-chloro-2-(4-methylphenylsulphonyl)-5-nitrothiazole are obtained. The compound can be recrystallized from cyclohexane and can be sublimed at 140° C./0.1 mbar. Melting point 153° C. to 153.5° C.

EXAMPLE 13

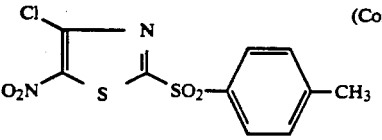

(Compound No. 66)

15.65 g (0.09 mol) of 3-chloroperxybenzoic acid are added to a solution of 5.73 g (0.02 mol) of 4-chloro-2-(4-methylphenylmercapto)-5-nitrothiazole (compound No. 57 according to the invention) in 200 ml of methylene chloride and the mixture is stirred under reflux for 8 hours. After cooling, the 3-chlorobenzoic acid which has precipitated is first filtered off. The filtrate is concentrated to dryness at a room temperature in vacuo and the residue which remains is stirred intensively with excess aqueous sodium bicarbonate solution, filtered off, washed with water and dried. 6.2 g (97.3% of theory) of 4-chloro-2-(4-methylphenylsulphonyl)-5-nitrothiazole, which is identical in all its properties to the compound obtained in Example 12 are obtained.

EXAMPLE 14

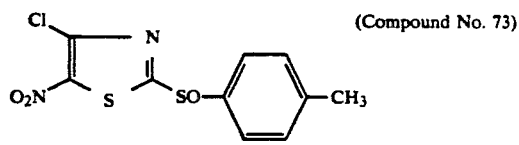
(Compound No. 73)

A total of 4.35 g (0.025 mol) of 3-chloroperoxybenzoic acid are added in portions (about 8 portions) to a solution of 5.2 g (0.018 mol) of 4-chloro-2-(4-methylphenylmercapto)-5-nitrothiazole (compound No. 57 according to the invention) in 200 ml of methylene chloride at room temperature in the course of about 50 hours. The mixture is then concentrated to dryness in vacuo at room temperature and the residue which remains is stirred intensively with excess aqueous sodium bicarbonate solution, filtered off, washed with water and dried. 4-Chloro-2-(4-methylphenylsulphinyl)-5-nitrothiazole of melting point 112° C. (from cyclohexane) is obtained.

EXAMPLE 15

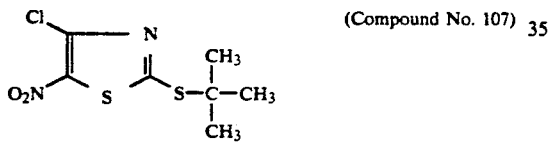
(Compound No. 107)

Compound No. 107 is prepared analogously to Example 2 from 2,4-dichloro-5-nitrothiazole and t-butylmercaptan. The oil formed after stirring the mixture into excess icewater is taken up in methylene chloride and the methylene chloride phase is separated off, dried with anhydrous sodium sulphate and concentrated in vacuo. Excess 2,4-dichloro-5-nitrothiazole is removed by high vacuum distillation in a flash distillation apparatus up to a heating bath temperature of 70° C. under 0.1 mbar and pure 2-tert.-butylmercapto-4-chloro-5-nitrothiazole is then distilled at a heating bath temperature of about 80° C./0.1 mbar.

EXAMPLE 16

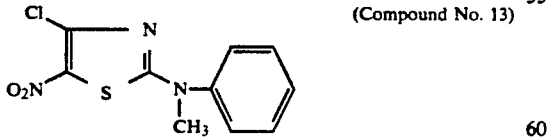
(Compound No. 13)

12.7 g (0.105 mol) of N,N-dimethylaniline are added to a solution of 19.9 g (0.1 mol) of 2,4-dichloro-5-nitrothiazole in 250 ml of acetonitrile and the reaction mixture is stirred under reflux for 75 hours. The solvent is then stripped off in vacuo and the solid residue is stirred into water, filtered off, washed with water and dried. 25.8 g (95.7 % of theory) of 4-chloro-2-(N-methyl-N-phenylamino)-5-nitrothiazole are obtained. The compound can be recrystallized from cyclohexane and can be sublimed at about 110° C. to 120° C./0.1 mbar. Melting point 136° C. to 137° C.

It is also possible to prepare compound No. 13 analogously to Example 2.

PREPARATION OF STARTING SUBSTANCES WHICH ARE NOT YET KNOWN FROM THE LITERATURE

EXAMPLE A1

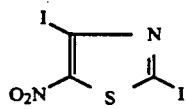

19.9 g (0.1 mol) of 2,4-dichloro-5-nitrothiazole are dissolved in 500 ml of acetone and, after addition of 150 g (1 mol) of sodium iodide, the mixture is stirred under reflux for about 60 hours. Thereafter, the content of 2,4-diiodo-5-nitrothiazole in the reaction mixture is more than 95%, according to analysis by gas chromatography. The solvent is then stripped off in vacuo and the residue is stirred into water, filtered off, washed with water and dried. 33.9 g (89% of theory) of 2,4-diiodo-5-nitrothiazole of melting point 135° C. are obtained after recrystallization from cyclohexane.

EXAMPLE A2

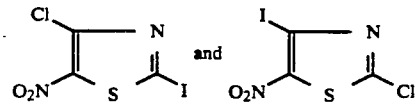

39.8 g (0.2 mol) of 2,4-dichloro-5-nitrothiazole are dissolved in 500 ml of acetone and, after addition of 90 g (0.6 mol) of sodium iodide, the mixture is stirred at room temperature for about 6 days, the progress of the reaction being monitored by gas chromatography. The solvent is then stripped off in vacuo and the residue is stirred into water, filtered off, washed with water and dried. A substance mixture which, according to analysis by gas chromatography, contains 71.5% of 2-iodo-4-chloro-5-nitrothiazole and 25.8% of 2-chloro-4-iodo-5-nitrothiazole is obtained. HPLC (=high pressure liquid chromatography) chromatographic separation gave the pure substances with the following melting points:

2-iodo-4-chloro-5-nitrothiazole: melting point 80° C.-81° C., 2-chloro-4-iodo-5-nitrothiazole: melting point 108° C.-109.5° C.

EXAMPLE A3

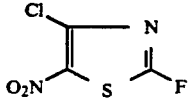

19.9 g (0.1 mol) of 2,4-dichloro-5-nitrothiazole are dissolved in 60 ml of acetonitrile and, after addition of 24 g (0.4 mol) of calcined potassium fluoride and 0.5 g of [18] crown-6, the mixture is stirred at room temperature for about one week, the progress of the reaction being monitored by gas chromatography. The crude batch is distilled under 0.1 to 0.2 mbar at a temperature of 20° to 25° C., the volatile constituents being collected in a receiver cooled with methanol/dry ice. The acetonitrile is then distilled off under normal pressure, a mixture of approximately equal parts of 4-chloro-2-fluoro-5-nitrothiazole and 2,4-dichloro-5-nitrothiazole remaining. The 4-chloro-2-fluoro-5-nitrothiazole can be separated off from this mixture, for example, by fractional distillation.

$^{19}$F-NMR (CDCl$_3$) (CF$_3$-COOH as the external standard): = −17.5 ppm.

| MS: | 182 (37%) = M$^+$ = C$_3$ClFN$_2$O$_2$S |
|---|---|
| | 124 (34%) |
| | 91 (60%) |
| | 63 (100%) |

The isomeric 2-chloro-4-fluoro-5-nitrothiazole can be identified by gas chromatography as a secondary component in a relative amount of between 1 and 5%, based on the 4-chloro-2-fluoro-5-nitrothiazole.

$^{19}$F-NMR (CDCL$_3$) (CF$_3$-COOH as the external standard): = −22.7 ppm.

| MS: | 182 (83%) = M$^+$ = C$_3$ClFN$_2$O$_2$S |
|---|---|
| | 136 (32%) |
| | 91 (43%) |
| | 75 (100%) |

The following 4-halogeno-5-nitrothiazole derivatives of the general formula (I) are obtained in a corresponding manner and in accordance with the general instructions on the preparation.

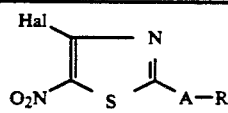

(I)

| Compound Number | Hal | —A— | —R | Melting Point (°C.) (recrystallized from) | Preparation |
|---|---|---|---|---|---|
| 1 | Cl | —N(C$_2$H$_5$)— | —C$_2$H$_5$ | 85 (Cyclohexane) | see Example 3 |
| 2 | Cl | | —A—R = —N(morpholino) | 135 (Ethanol) | analogously to Example 3 |
| 3 | Cl | —NH— | H | 180 decomposition | see Example 5 |
| 4 | Cl | | —A—R = —N(1,2,4-triazolyl) | 122 (Cyclohexane) | analogously to Example 6 |
| 5 | Cl | —NH— | phenyl | 190-1 decomposition | analogously to Example 1 and see Example 4 |
| 6 | Cl | | —A—R = —N(pyrazolyl) | 147 (Cyclohexane) | analogously to Example 6 |
| 7 | Cl | | —A—R = —N(imidazolyl) | 150 decomposition | analogously to Example 6 |
| 8 | Cl | —NH— | 4-Cl-phenyl | 207 decomposition | analogously to Example 4 |
| 9 | Cl | —O— | 4-Cl-phenyl | 94 (Methanol) | analogously to Example 2 |

-continued $$\text{(I)}$$

| Compound Number | Hal | —A— | —R | Melting Point (°C.) (recrystallized from) | Preparation |
|---|---|---|---|---|---|
| 10 | Cl | —NH— | —C₆H₄—OCF₃ (para) | 121 | analogously to Example 1 |
| 11 | Cl | | —A—R = —N=C(CH₃)—CH=CH—N (cis ring) | 153 | see Example 6 |
| 12 | Cl | | —A—R = —N=C(CH₃)—CH=C(CH₃)—N | 205 | analogously to Example 6 |
| 13 | Cl | —N(CH₃)— | phenyl | 136-7 Cyclohexane | analogously to Example 2 and see Example 16 |
| 14 | Cl | —N(C₂H₅)— | phenyl | 93-4 Cyclohexane | analogously to Example 2 |
| 15 | Cl | —N(C₂H₅)— | 3-methylphenyl | 81 | analogously to Example 2 |
| 16 | Cl | —N(CH₃)— | 4-chlorophenyl | 118-20 | analogously to Example 1 |
| 17 | Cl | —O— | H | 136 | see Example 7 present as (tautomer shown) |
| 18 | Cl | —NH— | —CH₂—phenyl | 195-6 decomposition | see Example 8 |
| 19 | Cl | —NH— | cyclohexyl | 130-1 (Cyclohexane) | analogously to Example 2 |
| 20 | Cl | —N(CH₃)— | —CH₂—phenyl | 112-3 (Cyclohexane) | analogously to Example 2 |
| 21 | Cl | —NH— | —C(CH₃)₃ | 175-6 (Acetonitrile) | analogously to Example 2 |

-continued

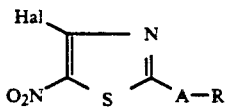
(I)

| Compound Number | Hal | —A— | —R | Melting Point (°C.) (recrystallized from) | Preparation |
|---|---|---|---|---|---|
| 22 | Cl | —NH— | 2-Cl-phenyl | 151 decomposition | analogously to Example 1 |
| 23 | Cl | —NH— | 3-Cl-phenyl | 197 decomposition | analogously to Example 1 |
| 24 | Cl | —NH— | 2,3-di-Cl-phenyl | 108–11 | analogously to Example 1 |
| 25 | Cl | —NH— | 2,4-di-Cl-phenyl | 188–9 decomposition | analogously to Example 1 |
| 26 | Cl | —NH— | 2,5-di-Cl-phenyl | 136–8 decomposition | analogously to Example 1 |
| 27 | Cl | —NH— | 3,4-di-Cl-phenyl | 214–5 decomposition | analogously to Example 1 |
| 28 | Cl | —NH— | 3,5-di-Cl-phenyl | 142–4 decomposition | analogously to Example 1 |
| 29 | Cl | —N(Ph)— | phenyl | decomposition 171–3 | analogously to Example 10 |
| 30 | Cl | —NH— | 4-CH₃-phenyl | 194 decomposition | analogously to Example 1 |

-continued

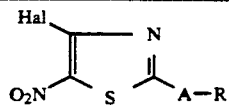
(I)

| Compound Number | Hal | —A— | —R | Melting Point (°C.) (recrystallized from) | Preparation |
|---|---|---|---|---|---|
| 31 | Cl | —NH— | 3-methylphenyl | 175 | analogously to Example 1 |
| 32 | Cl | —NH— | 2,5-dimethylphenyl | 177–8 decomposition | analogously to Example 1 |
| 33 | Cl | —NH— | 3,5-dimethylphenyl | 179–80 decomposition | analogously to Example 1 |
| 34 | Cl | —NH— | 2,6-dimethylphenyl | 215–6 decomposition | analogously to Example 1 |
| 35 | Cl | —NH— | 3,4,5-trimethylphenyl | 183–5 decomposition | analogously to Example 1 |
| 36 | Cl | —NH— | 2,3-dimethylphenyl | 202 decomposition | analogously to Example 1 |
| 37 | Cl | —N(CH3)— | 3,4-dichlorophenyl | 123–4 | analogously to Example 1 |
| 38 | Cl | —NH— | 2,3,6-trimethylphenyl | 216–7 decomposition | analogously to Example 1 |
| 39 | Cl | —NH— | 2,3,4,6-tetramethylphenyl | 170 decomposition | analogously to Example 1 |

-continued

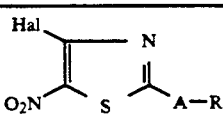
(I)

| Compound Number | Hal | —A— | —R | Melting Point (°C.) (recrystallized from) | Preparation |
|---|---|---|---|---|---|
| 40 | Cl | —NH— | pentamethylphenyl (2,3,4,5,6-pentamethyl) | 243-4 decomposition | analogously to Example 1 |
| 41 | Cl | —NH— | 4-methoxyphenyl | 193 decomposition | analogously to Example 4 |
| 42 | I | —NH— | phenyl | 168-9 decomposition (Cyclohexane) | analogously to Example 1 (from 2,4-Diiodo-5-nitrothiazole) |
| 43 | Cl | —NH— | 2-methoxyphenyl | 185-6 decomposition | analogously to Example 1 |
| 44 | Cl | —NH— | 3-methoxyphenyl | 175-6 decomposition | analogously to Example 1 |
| 45 | Cl | —O— | —CH₃ | 52 (petroleum ether) | see Example 9 |
| 46 | Cl | —NH— | 3,4-dimethylphenyl | 178-9 decomposition | analogously to Example 1 |
| 47 | Cl | —NH— | 4-nitrophenyl | 262-3 decomposition | analogously to Example 1 |
| 48 | Cl | —N(C₂H₅)— | 2-methylphenyl | Oil | analogously to Example 1 |
| 49 | Cl | —NH— | 3-methylphenyl | 180-1 decomposition | analogously to Example 1 |
| 50 | Cl | —NH— | 4-bromophenyl | 208 decomposition | analogously to Example 1 |

-continued

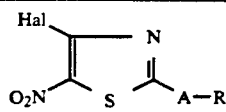
(I)

| Compound Number | Hal | —A— | —R | Melting Point (°C.) (recrystallized from) | Preparation |
|---|---|---|---|---|---|
| 51 | Cl | —NH— | 3-Br-phenyl | 191-2 decomposition | see Example 1 |
| 52 | Cl | —O— | phenyl | 96 (Petroleum ether) | see Example 2 |
| 53 | Cl | —O— | 3,4-dichlorophenyl | 83-4 | analogously to Example 2 |
| 54 | Cl | —O— | 4-CH₃-phenyl | 94-6 | analogously to Example 2 |
| 55 | Cl | —O— | 4-OCH₃-phenyl | 107-8 | analogously to Example 2 |
| 56 | Cl | —S— | phenyl | 87-9 | analogously to Example 2 |
| 57 | Cl | —S— | 4-CH₃-phenyl | 83-5 | analogously to Example 2 |
| 58 | Cl | —S— | 4-Cl-phenyl | 93 | analogously to Example 2 |
| 59 | Cl | —N(CH₂-phenyl)— | —CH₂-phenyl | 94 (Cyclohexane) | analogously to Example 2 |
| 60 | Cl | —N(C₂H₅)— | naphthyl | 240 decomposition | analogously to Example 2 |

-continued

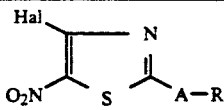
(I)

| Compound Number | Hal | —A— | —R | Melting Point (°C.) (recrystallized from) | Preparation |
|---|---|---|---|---|---|
| 61 | Cl | —NH— | 1-naphthyl | 178-9 decomposition | analogously to Example 1 |
| 62 | Cl | —NH— | 4-(N,N-dimethylamino)phenyl | >260 | analogously to Example 1 |
| 63 | Cl | —NH— | —CH(CH₃)–phenyl | 108 (Cyclohexane) | analogously to Example 4 |
| 64 | Cl | —S— | 4-methoxyphenyl | 62-5 | analogously to Example 2 |
| 65 | Cl | —N(CH₃)— | —CH₃ | 182.5 | analogously to Example 3 |
| 66 | Cl | —SO₂— | 4-methylphenyl | 153-153.5 (Cyclohexane) | see Examples 12 and 13 |
| 67 | Cl |  | —A—R = —N(pyrrolyl) | 138-9 (Toluene) | see Example 10 |
| 68 | Cl | —NH— | —CH₃ | 212 (Z.) (Methanol) | see Example 11 |
| 69 | Cl | —NH— | 2,5-dimethylphenyl | 186-7 decomposition | analogously to Example 1 |
| 70 | Cl | —NH— | 2,4,6-trimethylphenyl | 214-5 decomposition | analogously to Example 1 |
| 71 | Cl | —NH— | 2,5-dimethoxyphenyl | 167-9 decomposition | analogously to Example 1 |

-continued

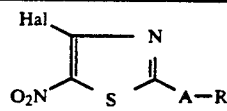

(I)

| Compound Number | Hal | —A— | —R | Melting Point (°C.) (recrystallized from) | Preparation |
|---|---|---|---|---|---|
| 72 | Cl | —NH— | 2-methyl-4-methoxyphenyl (CH₃O, OCH₃) | 153–4 decomposition | analogously to Example 1 |
| 73 | Cl | —SO— | 4-CH₃-phenyl | 112 | see Example 14 |
| 74 | Cl | —NH— | 2,4,6-tri-CH₃-phenyl | 208–9 decomposition | analogously to Example 1 |
| 75 | Cl | —O— | 4-C(CH₃)₃-phenyl | 87–8 | analogously to Example 2 |
| 76 | Cl | —O— | 4-F-phenyl | 103–4 | analogously to Example 2 |
| 77 | Cl | —O— | 2-Cl-phenyl | 79–80 | analogously to Example 2 |
| 78 | Cl | —O— | 3-Cl-phenyl | 43 | analogously to Example 2 |
| 79 | Cl | —O— | 3-NO₂-phenyl | 106–7 | analogously to Example 2 |
| 80 | Cl | —O— | 2-CH₃-phenyl | Oil | analogously to Example 2 |
| 81 | Cl | —O— | 4-NO₂-phenyl | 147–8 | analogously to Example 2 |

-continued

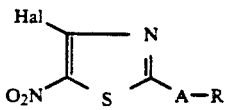
(I)

| Compound Number | Hal | —A— | —R | Melting Point (°C.) (recrystallized from) | Preparation |
|---|---|---|---|---|---|
| 82 | Cl | —O— | 3-methylphenyl | 44-5 | analogously to Example 2 |
| 83 | Cl | —O— | 2,3-dimethylphenyl | 76-7 | analogously to Example 2 |
| 84 | Cl | —S— | 4-tert-butylphenyl | Oil | analogously to Example 2 |
| 85 | Cl | —O— | 2,5-dimethylphenyl | 54 | analogously to Example 2 |
| 86 | Cl | —O— | 2,4,6-trimethylphenyl | 98 | analogously to Example 2 |
| 87 | Cl | —O— | 2,6-di-tert-butylphenyl | 188-9 | analogously to Example 2 |
| 88 | Cl | —NH— | 3-isopropoxyphenyl | 48-9 | analogously to Example 1 |
| 89 | Cl | —O— | 4-(methylthio)phenyl | 96 | analogously to Example 2 |
| 90 | Cl | —O— | naphthyl | 51-2 | analogously to Example 2 |

-continued

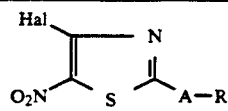
(I)

| Compound Number | Hal | —A— | —R | Melting Point (°C.) (recrystallized from) | Preparation |
|---|---|---|---|---|---|
| 91 | Cl | —O— | 2,6-dimethylphenyl (CH₃, CH₃) | 45 | analogously to Example 2 |
| 92 | Cl | —O— | 2,6-dimethylphenyl (CH₃, CH₃) | Oil | analogously to Example 2 |
| 93 | Cl | —O— | 3,5-dimethylphenyl (CH₃, CH₃) | 57 | analogously to Example 2 |
| 94 | Cl | —O— | 2,5-dimethylphenyl (CH₃, CH₃) | 61 | analogously to Example 2 |
| 95 | Cl | —NH— | 2,4,5-trichlorophenyl (Cl, Cl, Cl) | 191-2 | analogously to Example 1 |
| 96 | Cl | —NH— | 4-(CH₃SO₂NH)phenyl | 203 | analogously to Example 1 |
| 97 | Cl | —NH— | 2-CF₃-4-NO₂-phenyl | 226-7 decomposition | analogously to Example 1 |
| 98 | Cl | —NH— | 2-CF₃-4-Cl-phenyl | 124-5 decomposition | analogously to Example 1 |
| 99 | Cl | —NH— | 2-F-phenyl | 157-8 decomposition | analogously to Example 1 |

-continued

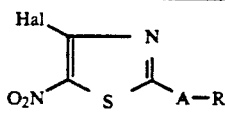
(I)

| Compound Number | Hal | —A— | —R | Melting Point (°C.) (recrystallized from) | Preparation |
|---|---|---|---|---|---|
| 100 | Cl | —NH— | 4-F-phenyl | 112-3 decomposition | analogously to Example 1 |
| 101 | Cl | —NH— | 3-SCF₃-phenyl | 77-8 | analogously to Example 1 |
| 102 | Cl | —NH— | 3-I-phenyl | 158-9 decomposition | analogously to Example 1 |
| 103 | Cl | —NH— | 3-NO₂-phenyl | 163-4 decomposition | analogously to Example 1 |
| 104 | Cl | —O— | 2-naphthyl | 128 | analogously to Example 2 |
| 105 | Cl | —O— | 4-biphenyl | 187 | analogously to Example 2 |
| 106 | Cl | —S— | —CH(CH₃)₂ | Oil | analogously to Example 15 |
| 107 | Cl | —S— | —C(CH₃)₃ | Oil | see Example 15 |
| 108 | Cl | —S— | 4-F-phenyl | 95 | analogously to Example 2 |
| 109 | Cl | —O— | 2-COOCH₃-phenyl | 56 | analogously to Example 2 |

-continued

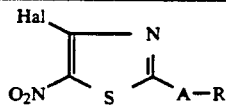
(I)

| Compound Number | Hal | —A— | —R | Melting Point (°C.) (recrystallized from) | Preparation |
|---|---|---|---|---|---|
| 110 | Cl | —O— | 3-fluorophenyl | 67 | analogously to Example 2 |
| 111 | I | —N(CH₃)— | phenyl | 86-8 decomposition | analogously to Example 2 from 2-Chloro-4-iodo-5-nitrothiazole |
| 112 | Br | —N(CH₃)— | phenyl | 102-4 decomposition | analogously to Example 1 |
| 113 | Cl | —N(H)— | —CH₂—CH=CH₂ | 130 | analogously to Example 1 |
| 114 | Cl | —N(H)— | 2,6-dichlorophenyl | 141 (Petroleum ether) | in Tetrahydrofuran with addition of sodium hydride |
| 115 | Cl | —N(CH₂—CH=CH₂)— | —CH₂—CH=CH₂ | Oil | analogously to Example 1 |
| 116 | Cl | —N(H)— | 3-(CF₃)phenyl | 121-2 | analogously to Example 1 |
| 117 | Cl | —N(C₂H₅)— | 3-nitrophenyl | 157-8 decomposition | analogously to Example 1 |
| 118 | Cl | —N(H)— | 3-(N(CH₃)₂)phenyl | 169-70 decomposition | analogously to Example 1 |
| 119 | Cl | —N(H)— | —C(CH₃)₂—phenyl | 71-2 decomposition | analogously to Example 2 |
| 120 | Cl | —N(H)— | 4-(CONH₂)phenyl | 259 decomposition | analogously to Example 1 |

-continued $$\underset{O_2N}{\overset{Hal}{\diagup}}\underset{S}{\diagdown}\underset{}{\overset{N}{\diagdown}}A-R \qquad (I)$$

| Compound Number | Hal | —A— | —R | Melting Point (°C.) (recrystallized from) | Preparation |
|---|---|---|---|---|---|
| 121 | Cl | —NH— | 4-(C(=O)CH$_3$)-phenyl | 262-3 decomposition | analogously to Example 1 |
| 122 | Cl | —NH— | 4-SO$_2$NH$_2$-phenyl | >280 | analogously to Example 1 |
| 123 | Cl | —NH— | 4-CN-phenyl | 266-7 decomposition | analogously to Example 1 |
| 124 | Cl | —NH— | 4-CF$_3$-phenyl | 202-3 decomposition | analogously to Example 1 |
| 125 | Cl | —NH— | —C(CH$_3$)$_2$—CN | 127-8 | analogously to Example 1 |
| 126 | Cl | —N(—(CH$_2$)$_3$—CN)— | —CH$_2$—CH$_2$—CN | 176 decomposition | analogously to Example 1 |
| 127 | Cl | —NH— | 4-O—C$_4$H$_9$-phenyl | 154-5 decomposition | analogously to Example 1 |
| 128 | Cl | —NH— | 4-CH(CH$_3$)$_2$-phenyl | 161-2 decomposition | analogously to Example 1 |
| 129 | Cl | —O— | 4-COOCH$_3$-phenyl | 124-5 | analogously to Example 2 |
| 130 | Cl | —O— | 2-COOC$_2$H$_5$-phenyl | 111-2 | analogously to Example 2 |
| 131 | Cl | —NH— | 4-cyclohexyl-phenyl | 185-6 decomposition | analogously to Example 1 |
| 132 | Cl | —NH— | 4-C$_2$H$_5$-phenyl | 174-5 decomposition | analogously to Example 1 |

-continued

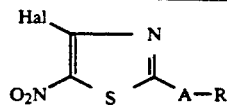
(I)

| Compound Number | Hal | —A— | —R | Melting Point (°C.) (recrystallized from) | Preparation |
|---|---|---|---|---|---|
| 133 | Cl | —N—H | 4-(SO₂—CH₃)phenyl | 268-9 decomposition | analogously to Example 1 |
| 134 | Cl | —N—H | 4-(C(CH₃)₃)phenyl | 189-90 decomposition | analogously to Example 1 |
| 135 | Cl | —O— | 3-(COOC₂H₅)phenyl | 80 | analogously to Example 2 |
| 136 | Cl | —N—H | 3,5-bis(CF₃)phenyl | 151-2 decomposition | analogously to Example 1 |
| 137 | Cl | —N—H | 4-I-phenyl | 165-6 decomposition | analogously to Example 1 |
| 138 | Cl | —N—H | 4-(NH—CO—CH₃)phenyl | 226-7 decomposition | analogously to Example 1 |
| 139 | Cl | —N—H | 2-Br-phenyl | 157-8 decomposition | analogously to Example 1 |
| 140 | Cl | —S— | 2,3,4,5,6-pentachlorophenyl | 154-5 decomposition (Acetonitrile) | analogously to Example 2 |
| 141 | Cl | —N—H | —C(CH₃)₂—(CH₂)₃—CH₃ | Oil | analogously to Example 1 |
| 142 | Cl | —S— | 2,4-dimethylphenyl | 95 | analogously to Example 2 |

-continued

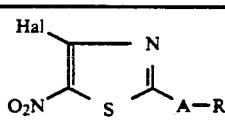
(I)

| Compound Number | Hal | —A— | —R | Melting Point (°C.) (recrystallized from) | Preparation |
|---|---|---|---|---|---|
| 143 | Cl | —S— | 2-Cl-phenyl | 52-3 | analogously to Example 2 |
| 144 | Cl | —S— | 4-Br-phenyl | 80-1 | analogously to Example 2 |
| 145 | Cl | —O— | 2,4-diCl-phenyl | 123-4 | analogously to Example 2 |
| 146 | Cl | —O— | 2,4,6-triBr-phenyl | 134-5 | analogously to Example 2 |
| 147 | Cl | —O— | 2,6-diCH₃-4-Cl-phenyl (3,5-diCH₃-4-Cl) | 75-6 | analogously to Example 2 |
| 148 | Cl | —S— | 2-NO₂-4-Cl-phenyl | 117-8 | analogously to Example 2 |
| 149 | Cl | —S— | 2-CH₃-phenyl | 96-97 | analogously to Example 2 |
| 150 | Cl | —O— | 3,5-diOCH₃-phenyl | Oil | analogously to Example 2 |
| 151 | Cl | —O— | 3-OCH₃-4-(CH=CH—CH₃)-phenyl | 57 | analogously to Example 2 |

-continued

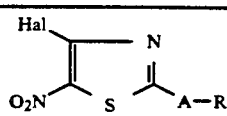
(I)

| Compound Number | Hal | —A— | —R | Melting Point (°C.) (recrystallized from) | Preparation |
|---|---|---|---|---|---|
| 152 | Cl | —O— | 4-C₂H₅-phenyl | 58-9 | analogously to Example 2 |
| 153 | Cl | —O— | 2,3,5,6-tetrachlorophenyl | 208-9 | analogously to Example 2 |
| 154 | Cl | —O— | 3-OCH₃-4-(CH₂—CH=CH₂)-phenyl | Oil | analogously to Example 2 |
| 155 | Cl | —O— | 4-I-phenyl | 98 | analogously to Example 2 |
| 156 | Cl | —O— | 2-Cl-4-OCH₃-phenyl | 83 | analogously to Example 2 |
| 157 | Cl | —O— | 3-CH₃-4-OCH₃-phenyl | 96 | analogously to Example 2 |
| 158 | Cl | —NH— | 2-N(CH₃)₂-3-CH₃-phenyl | 106-7 decomposition | analogously to Example 1 |
| 159 | Cl | —O— | 2-(CH₂—CH=CH₂)-phenyl | Oil | analogously to Example 2 |
| 160 | Cl | —O— | 4-Br-phenyl | 97 | analogously to Example 2 |
| 161 | Cl | —O— | 2,4-diCl-phenyl | 106 | analogously to Example 2 |

-continued

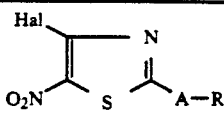
(I)

| Compound Number | Hal | —A— | —R | Melting Point (°C.) (recrystallized from) | Preparation |
|---|---|---|---|---|---|
| 162 | Cl | —O— | 2,3-dimethoxyphenyl (OCH₃, OCH₃) | 116 | analogously to Example 2 |
| 163 | Cl | —O— | 2-tert-butyl-5-methylphenyl | Oil | analogously to Example 2 |
| 164 | Cl | —O— | tetrafluorophenyl | 68 | analogously to Example 2 |
| 165 | Cl | —O— | 3-methoxyphenyl | 78 | analogously to Example 2 |
| 166 | Cl | —O— | 3-tert-butylphenyl | 68 | analogously to Example 2 |
| 167 | Cl | —O— | 3,5-dimethoxyphenyl | 115 | analogously to Example 2 |
| 168 | Cl | —O— | 2,4-dimethoxyphenyl | 152 | analogously to Example 2 |
| 169 | Cl | —O— | 4-isopropylphenyl | 86 | analogously to Example 2 |
| 170 | Cl | —O— | 2,4,6-trimethylphenyl | Oil | analogously to Example 2 |

-continued

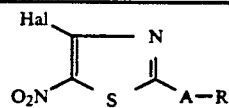
(I)

| Compound Number | Hal | —A— | —R | Melting Point (°C.) (recrystallized from) | Preparation |
|---|---|---|---|---|---|
| 171 | Cl | —O— | 2-methyl-4-tert-butylphenyl | Oil | analogously to Example 2 |
| 172 | Cl | —O— | 2-(1-propyl)phenyl | Oil | analogously to Example 2 |
| 173 | Cl | —O— | 2,3,4,5-tetrafluorophenyl | 52 | analogously to Example 2 |
| 174 | Cl | —SO₂— | phenyl | 125 decomposition | analogously to Example 13 |
| 175 | Cl | —O— | 2,4-dichlorophenyl | Oil | analogously to Example 2 |
| 176 | Cl | —O— | 2,5-dichlorophenyl | 122 | analogously to Example 2 |
| 177 | Cl | —O— | 2,3-dichlorophenyl | 113 | analogously to Example 2 |
| 178 | Cl | —O— | 3-methyl-4-chlorophenyl | 86 | analogously to Example 2 |
| 179 | Cl | —O— | 2-chloro-3-methylphenyl | Oil | analogously to Example 2 |
| 180 | Cl | —N(H)— | 3-methyl-4-methoxyphenyl | 144 decomposition | analogously to Example 1 |

-continued

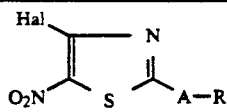
(I)

| Compound Number | Hal | —A— | —R | Melting Point (°C.) (recrystallized from) | Preparation |
|---|---|---|---|---|---|
| 181 | Cl | H —N— | 2-Cl, 4-CH₃-phenyl | 162-3 decomposition | analogously to Example 1 |
| 182 | Cl | H —N— | 2-Cl, 4-OCH₃-phenyl | 148 decomposition | analogously to Example 1 |
| 183 | Cl | H —N— | 2-CH₃, 4-Cl-phenyl | 201-2 decomposition | analogously to Example 1 |
| 184 | Cl | H —N— | 2-F, 4-Cl-phenyl | 205-6 decomposition | analogously to Example 1 |
| 185 | Cl | H —N— | 2-Cl, 4-F-phenyl | 168-9 decomposition | analogously to Example 1 |
| 186 | Cl | H —N— | 4-SCF₃-phenyl | 126 decomposition | analogously to Example 1 |
| 187 | Cl | H —N— | 2,4-F₂-phenyl | 117 decomposition | analogously to Example 1 |
| 188 | Cl | —N— \| CH₃ | 2-CH₃, 4-Cl-phenyl | 140-1 decomposition | analogously to Example 1 |
| 189 | Cl | H —N— | 3-SCF₃-phenyl | 126-7 decomposition | analogously to Example 1 |
| 190 | Cl | —N— \| CH₃ | 2,3-(CH₃)₂-phenyl | 179-80 decomposition | analogously to Example 1 |

-continued

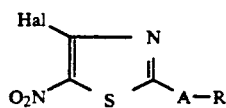
(I)

| Compound Number | Hal | —A— | —R | Melting Point (°C.) (recrystallized from) | Preparation |
|---|---|---|---|---|---|
| 191 | Cl | H —N— | —CH(CH₃)—C₆H₄—Cl (4-Cl) | Oil | analogously to Example 1 |
| 192 | Cl | H —N— | 3,4,5-trichlorophenyl | 221 decomposition | analogously to Example 1 |
| 193 | Cl | H —N— | 3,4,5-trimethoxyphenyl | 177–8 decomposition | analogously to Example 1 |
| 194 | Cl | H —N— | 3,4-dimethoxyphenyl | 201 decomposition | analogously to Example 1 |
| 195 | Cl | CH₃ —N— | 3-CF₃-phenyl | 94–5 | analogously to Example 1 |
| 196 | Cl | C₂H₅ —N— | 3-Cl-phenyl | 87–8 | analogously to Example 1 |
| 197 | Cl | C₂H₅ —N— | 2-OC₂H₅-phenyl | 71 | analogously to Example 1 |
| 198 | Cl | CH₃ —N— | 4-OCH₃-phenyl | 141 decomposition | analogously to Example 1 |
| 199 | Cl | C₂H₅ —N— | 3,4-dichlorophenyl | 144 decomposition | analogously to Example 1 |

-continued

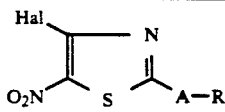
(I)

| Compound Number | Hal | —A— | —R | Melting Point (°C.) (recrystallized from) | Preparation |
|---|---|---|---|---|---|
| 200 | Cl | H —N— | 3,5-dimethoxyphenyl (OCH₃, OCH₃) | 97–8 decomposition | analogously to Example 1 |
| 201 | Cl | H —N— | phenyl-COOCH₃ | 161–2 decomposition | analogously to Example 1 |
| 202 | Cl | H —N— | phenyl-CN | 224–5 decomposition | analogously to Example 1 |
| 203 | Cl | H —N— | Cl, CF₃-phenyl | 159–60 decomposition | analogously to Example 1 |
| 204 | Cl | H —N— | CH₃, Cl-phenyl | 204–5 decomposition | analogously to Example 1 |
| 205 | Cl | H —N— | CH₃, NO₂-phenyl | 213–4 decomposition | analogously to Example 1 |
| 206 | Cl | H —N— | Cl, CH₃-phenyl | 161–2 decomposition | analogously to Example 1 |
| 207 | Cl | H —N— | NO₂, CH₃-phenyl | 209 decomposition | analogously to Example 1 |
| 208 | Cl | | —A—R = —N(pyrrolidinyl) | 162–3 decomposition | analogously to Example 3 |

-continued

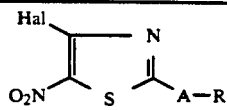
(I)

| Compound Number | Hal | —A— | —R | Melting Point (°C.) (recrystallized from) | Preparation |
|---|---|---|---|---|---|
| 209 | Cl | | —A—R = —N⟨piperidine⟩ | 91-2 | analogously to Example 3 |
| 210 | Cl | | —A—R = —N⟨azocane⟩ | 113 decomposition | analogously to Example 3 |
| 211 | Cl | —N(H)— | 4-Cl, 2-CF$_3$-phenyl | 167-8 decomposition | analogously to Example 1 |
| 212 | Cl | —N(H)— | 3-NHCHO-phenyl | 256 decomposition | analogously to Example 1 |
| 213 | Cl | —N(H)— | 3-phenoxyphenyl | 83 | analogously to Example 1 |
| 214 | Cl | —N(CH$_3$)— | 2-COOCH$_3$-phenyl | 112-3 | analogously to Example 1 |
| 215 | Cl | —N(H)— | 4-COOCH$_3$-phenyl | 254 decomposition | analogously to Example 1 |
| 216 | Cl | —N(H)— | 4-C$_{12}$H$_{25}$-phenyl | Oil | analogously to Example 1 |
| 217 | Cl | —N(H)— | 4-N(CH$_3$)(CHO)-phenyl | 221 decomposition | analogously to Example 1 |
| 218 | Cl | —N(H)— | 2,5-di-CH(CH$_3$)$_2$-phenyl | 228 decomposition | analogously to Example 1 |

-continued

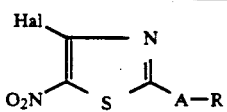
(I)

| Compound Number | Hal | —A— | —R | Melting Point (°C.) (recrystallized from) | Preparation |
|---|---|---|---|---|---|
| 219 | Cl | H<br>—N— | 4-(NH—CHO)-phenyl | 168-9 decomposition | analogously to Example 1 |
| 220 | Cl | H<br>—N— | 3,5-bis(COOCH₃)-phenyl | 117-8 decomposition | analogously to Example 1 |
| 221 | Cl | H<br>—N— | 2-CH₃-3-NO₂-phenyl | 156-7 decomposition | analogously to Example 1 |
| 222 | Cl | H<br>—N— | 2-CH₃-4-Cl-phenyl | 202 decomposition | analogously to Example 1 |
| 223 | Cl | H<br>—N— | 2-Cl-4-CH₃-phenyl | 186-7 decomposition | analogously to Example 1 |
| 224 | Cl | H<br>—N— | 2-CH₃-4-N(CH₃)₂-phenyl | 163-4 decomposition | analogously to Example 1 |
| 225 | Cl | H<br>—N— | 2-Cl-4-CH₃-phenyl (2,6-dimethyl variant) | 156-7 decomposition | analogously to Example 1 |
| 226 | Cl | H<br>—N— | 2-NO₂-4-Cl-phenyl | 148-9 decomposition | analogously to Example 1 |

-continued

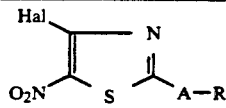
(I)

| Compound Number | Hal | —A— | —R | Melting Point (°C.) (recrystallized from) | Preparation |
|---|---|---|---|---|---|
| 227 | Cl | H —N— | 2,4-dimethyl-5-nitrophenyl (CH₃, CH₃, NO₂) | 230 decomposition | analogously to Example 1 |
| 228 | Cl | H —N— | 2-chloro-4-(methylthio)phenyl (Cl, SCH₃) | 159–60 decomposition | analogously to Example 1 |
| 229 | Cl | —O— | 2,6-di-tert-butyl-4-bromophenyl (C(CH₃)₃, Br, C(CH₃)₃) | 247 | analogously to Example 2 |
| 230 | Cl | H —N— | 2-chloro-4-nitrophenyl (Cl, NO₂) | 198–9 decomposition | analogously to Example 1 |
| 231 | Cl | C₂H₅ —N— | 2-methyl-4-nitrophenyl (CH₃, NO₂) | 149–50 decomposition | analogously to Example 1 |
| 232 | Cl | H —N— | —C₂H₅ | 167–8 decomposition | analogously to Example 11 |
| 233 | Cl | H —N— | —CH₂—C₂H₅ | 106 decomposition | analogously to Example 11 |
| 234 | Cl | H —N— | —CH(CH₃)₂ | 125–7 decomposition | analogously to Example 11 |
| 235 | Cl | H —N— | —CH₂—CH₂—OCH₃ | 124–8 | analogously to Example 11 |
| 236 | Cl | H —N— | —CH₂—CH₂—Cl | 143–4 decomposition | analogously to Example 11 |
| 237 | Cl | —S— | 4-nitrophenyl (NO₂) | 97–8 decomposition | analogously to Example 2 |
| 238 | Cl | —O— | 4-carbamoylphenyl (C(=O)NH₂) | 136–7 | analogously to Example 2 |

-continued $$\begin{array}{c} \text{Hal} \\ \diagdown \\ \text{O}_2\text{N} \end{array} \begin{array}{c} \text{N} \\ \diagup \\ \text{S} \end{array} \text{A—R} \qquad (I)$$

| Compound Number | Hal | —A— | —R | Melting Point (°C.) (recrystallized from) | Preparation |
|---|---|---|---|---|---|
| 239 | Cl | —O— | 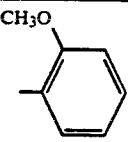 CH₃O— (ortho-methyl phenyl) | 186–7 decomposition | analogously to Example 2 |
| 240 | Cl | —O— | 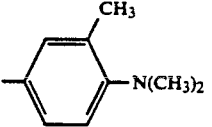 (2,4-dimethyl-N(CH₃)₂ phenyl) | 82 | analogously to Example 2 |
| 241 | Cl | —O— | 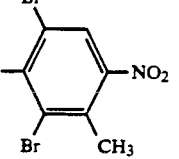 (3,5-dibromo-2,6-dimethyl-4-NO₂ phenyl) | 142 | analogously to Example 2 |
| 242 | Cl | —O— | 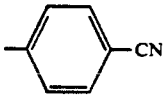 —⟨C₆H₄⟩—CN | 103–4 | analogously to Example 2 |
| 243 | Cl | —O— | 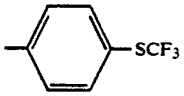 —⟨C₆H₄⟩—SCF₃ | 71 | analogously to Example 2 |
| 244 | Cl | —O— | 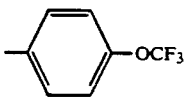 —⟨C₆H₄⟩—OCF₃ | 48 | analogously to Example 2 |
| 245 | Cl | —O— | 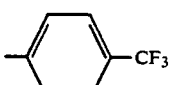 —⟨C₆H₄⟩—CF₃ | 77 | analogously to Example 2 |
| 246 | Cl | —O— | 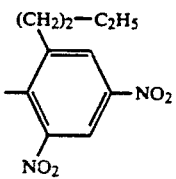 (CH₂)₂—C₂H₅, NO₂, NO₂ substituted phenyl | Oil | analogously to Example 2 |
| 247 | Cl | —O— | 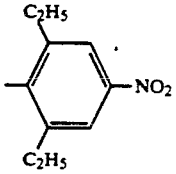 C₂H₅, NO₂, C₂H₅ substituted phenyl | 142 decomposition | analogously to Example 2 |
| 248 | Cl | —O— | 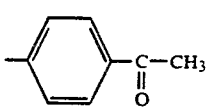 —⟨C₆H₄⟩—C(=O)—CH₃ | 108 | analogously to Example 2 |

-continued

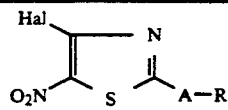

(I)

| Compound Number | Hal | —A— | —R | Melting Point (°C.) (recrystallized from) | Preparation |
|---|---|---|---|---|---|
| 249 | Cl | —O— | 2-COOCH₃, 4-NO₂ phenyl | 102-3 | analogously to Example 2 |
| 250 | Cl | —O— | 2-COOCH₃, 4-NO₂, 5-NO₂ phenyl | 104 | analogously to Example 2 |
| 251 | Cl | —O— | 4-NO₂, 3-(CH₃—N—SO₂—CH₃) phenyl | 159 | analogously to Example 2 |
| 252 | Cl | —O— | 2-Cl, 4-NO₂, 6-Cl phenyl | 145 | analogously to Example 2 |
| 253 | Cl | —O— | 2-(O=C—CH₃), 5-OCH₃ phenyl | 112 | analogously to Example 2 |
| 254 | Cl | —O— | 2-COOC₂H₅, 5-OCH₃ phenyl | 102 | analogously to Example 2 |
| 255 | Cl | —O— | 3-OCH₃, 4-OCH₃, 5-OCH₃ phenyl | 141 | analogously to Example 2 |
| 256 | Cl | —O— | 2-CH(CH₃)₂, 4-NO₂, 6-CH₃ phenyl | 104 | analogously to Example 2 |
| 257 | Cl | —O— | 2-COOC₂H₅, 4-NO₂, 6-NO₂ phenyl | 101 | analogously to Example 2 |

-continued (I)

| Compound Number | Hal | —A— | —R | Melting Point (°C.) (recrystallized from) | Preparation |
|---|---|---|---|---|---|
| 258 | Cl | —O— | (2,4-dinitro-3,5-dimethylphenyl) | 137 | analogously to Example 2 |
| 259 | Cl | —O— | (2-methoxy-4-nitrophenyl) | 129-30 | analogously to Example 2 |
| 260 | Cl | —O— | (2-methoxy-4,5-dinitrophenyl) | 149 | analogously to Example 2 |
| 261 | Cl | —O— | (2-cyano-4-nitrophenyl) | 128-9 | analogously to Example 2 |

USE EXAMPLES

The compounds shown below were employed as comparison substances in the use examples which follow:

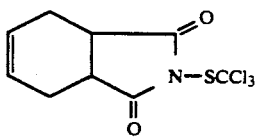

N-trichloromethylthio-tetrahydrophthalimide (compare U.S. Pat. No. 2,553,770);

(A)

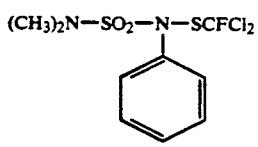   (B)

N,N-dimethyl-N'-phenyl-N'-(flourodichloromethylyhio)sulphamide (compare DAS (German Published Specification) 1,193,498) on

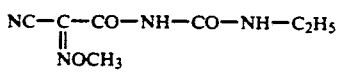   (C)

2-cyano-N-(ethylaminocarbonyl)-2-methoximino) -acetamide (compare U.S. Pat. No. 3,957,847) or

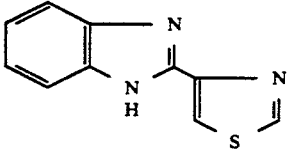

4-benzimidazol-2-yl-thiazole (compare R. Wegler "Chemmie der Planzenschutz-und Schadlingsbekäm pfungsmittel" (Chemical of Plant Protection Agents and Pesticides), Vol. 2, page 124, Springer-Verlag, Berlin, Heidelberg, N.Y. 1970),

EXAMPLE A

Venturia test (apple)/protective

Solvent: 4.7 parts by weight of acetone
Emulsifier: 0.3 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia*

*inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

At an active compound concentration of, for example, 5 ppm, many of the compounds according to the invention exhibit a degree of action of between 80 and 85% in comparison with the untreated control.

EXAMPLE B

Plasmopara test (vines)/protective

Solvent: 4.7 parts by weight of acetone
Emulsifier: 0.3 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the innoculation.

Many of the compounds according to the invention exhibit a degree of action of between 80 and 95% in comparison with the untreated control at an active compound concentration of 10 ppm.

EXAMPLE C

Phytophthora test (tomato)/protective

Solvent: 4.7 parts by weight of acetone
Emulsifier: 0.3 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and at about 20° C.

Evaluation is carried out 3 days after the inoculation.

At an active compound concentration of 10 ppm, many of the compounds according to the invention exhibit a degree of action of between 80 and 95% in comparison with the untreated control.

EXAMPLE D

Leptosphaeria nodorum test (wheat)/protective

Solvent: 100 parts by weight of dimethylformamide
Emulsifier: 0.25 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

At 0.025% by weight in the spray liquor, some of the compounds according to the invention exhibit a degree of action of 100% in comparison with the untreated control.

EXAMPLE E

In order to determine the activity against fungi on industrial materials, the minimum inhibitory concentrations (MIC) of active compounds according to the invention are determined:

An agar prepared from beerwort and peptone is treated with active compounds according to the invention at concentrations of from 0.1 mg/l to 5,000 mg/l. After solidification, the agar is contaminated with pure cultures of the test organisms listed in the table. After storage for 2 weeks at 28° C. and a relative atmospheric humidity of 60 to 70%, the MIC is determined. The MIC is the lowest concentration of active compound at which no infestation by the microbe species used takes place.

Thus, for example, compound Nos. 3, 6, 7, 9, 11, 45, 52, 53, 54, 55, 56, 64, 80, 77, 78 and 92 and also Examples A1 and A2 have a good action and a broad range of action in the case, for example, of the following test organisms:

*Alternaria tenuis*
*Aspergillus niger*
*Aureobasidium pullulans*
*Chaetomium globosum*
*Cladosporium cladosporioides*
*Lentinus tigrinus*
*Penicillium glaucum*
*Sclerophoma pityophila*
*Trichhoderma viride*

EXAMPLE F

Action against bacteria on industrial materials

An agar containing broth as the nutrient medium is treated with active compounds according to the invention at concentrations of from 1 to 5,000 ppm. The nutrient medium is then infected with each of the test organisms listed in the table given below, and the infected medium is kept for 2 weeks at 28° C. and a relative atmospheric humidity of 60 to 70%. The MIC is the lowest concentration of active compound at which no infestation by the microbe species used takes place.

TABLE

*Escherichia coli*
*Staphylococcus aureus*

In the case of these test organisms, the compounds 3, 6, 9, 53, 77, 78 and Examples A1 and A2, for example, exhibit a clearly superior action than the known comparative substance (D).

EXAMPLE G

A mixed culture of blue-green, brown and silicious algae (*Stichococcus bacillaris Naegeli, Euglena gracilis Klebs, Chlorella pyrenoidosa Chick, Phormidium foveolarum Gomont, Oscillatoria geminata Meneghini* and *Phaeodactylum tricornutum Bohlin*) is introduced into Allen's nutrient solution (Arch. Mikrobiol. 17, 34 to 15 (1952)) containing 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride per 4 l of sterile water, while air is bubbled through. After 2 weeks, the nutrient solution has become an intense green-blue color due to intensive algal growth. The dieing-off of the algae after active compounds according to the invention have been added can be seen from decoloration of the nutrient solution. Thus, for example, Examples A1 and A2 have a good action.

TABLE H

Action against slime organisms

Compounds according to the invention are used, dissolved in a little acetone, in concentrations of, in each case, 0.1 to 100 mg/l in Allen's nutrient solution (Arch. Mikrobiol. 17, 34 to 53 (1952) containing 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam in 4 l of sterile water. Shortly beforehand, the nutrient solution is infected with slime organisms (about $10^6$ organisms/ml) isolated from spinning water circuits used in the production of nylon. Nutrient solutions having the minimum inhibitory concentration (MIC) or greater active compound concentrations are still completely clear after culturing for 3 weeks at room temperature, i.e. notable degrees of multiplication of the microbes and slime formation do not occur in the active compound-free nutrient solutions after 3 to 4 days.

Thus, for example, the compound of Example A2 exhibits a very good action.

It will be appreciated that the instant specification and claims are set forth by way of illustration and not limitation, and that various modifications and changes may be made without departing from the spirit and scope of the present invention.

What is claimed is:

1. A 4-halogeno-5-nitrothiazole of the formula

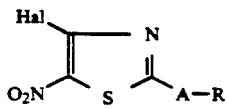

(I)

in which

Hal represents halogen,

A represents O, S, SO or SO$_2$, and

R represents alkyl, alkenyl or alkinyl, it being possible for the abovementioned radicals in each case to be optionally substituted by one or more identical or different substituents from the group consisting of halogen, alkoxy, aryloxy, alkylmercapto, arylmercapto and cyano, or represents cycloalkyl which optionally carries a fused-on ring and which is optionally substituted by one or more identical or different alkyl substituents, or represents aralkyl which is optionally substituted in the aryl part by one or more identical or different substituents from the group consisting of halogen, alkyl, halogenoalkyl, nitro, alkoxy, alkylmercapto and cyano, or represents aryl which is optionally substituted by one or more identical or different substituents from the group consisting of halogen, alkyl, alkenyl, alkinyl, halogenoalkyl, nitro, alkoxy, alkylmercapto, dialkylamino, carbalkoxy, carbamoyl, N-alkylcarbamoyl, N,N-dialkylcarbamoyl, halogenoalkyloxy, halogenoalkylmercapto, alkylsulphonylamino; alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cyclo-alkyl and cyano, the alkyl radicals having 1 to 12 carbon atoms, the alkenyl radicals having 3 to 12 carbon atoms, the alkinyl radicals having 4 to 12 carbon atoms, the cycloalkyl radicals having 3 to 8 carbon atoms, the aryl radicals having 6 to 12 carbon atoms, and the aralkyl radicals having 7 to 16 carbon atoms.

2. A 4-halogeno-5-nitrothiazole according to claim 1, in which

A—R represents OR, wherein

R represents alkyl, alkenyl or alkinyl, or represents cycloalkyl which optionally carries a fused-on ring and which is optionally substituted by one or more identical or different alkyl substituents, or for aralkyl which is optionally substituted in the aryl part by one or more identical or different substituents from the group consisting of halogen, alkyl, halogenoalkyl, nitro, alkoxy, alkylmercapto and cyano, or for aryl which is optionally substituted by one or more identical or different substituents from the group consisting of halogen, alkyl, alkenyl, halogenoalkyl, nitro, alkoxy, alkylmercapto, dialkylamino, carbalkoxy, carbamoyl, N-alkylcarbamoyl, N,N-dialkylcarbamoyl, halogenoalkoxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano, or A—R represents SR, wherein R represents alkyl, alkenyl or alkinyl, or represents cycloalkyl which is optionally substituted by one or more identical or different alkyl substituents, or represents aralkyl which is optionally substituted in the aryl part by one or more identical or different substituents from the group consisting of halogen, alkyl, halogenoalkyl, nitro, alkoxy, alkylmercapto and cyano, or represents aryl which is optionally substituted by one or more identical or different substituents from the group consisting of halogen, alkyl, alkenyl, halogenoalkyl, nitro, alkoxy, alkylmercapto, dialkylamino, carbalkoxy, carbamoyl, N-alkylcarbamoyl, N,N-dialkylcarbamoyl, halogenoalkoxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkoxy, aralkylmercapto, acylamino, acylalkylamino, cycloalkyl and cyano, or A—R represents SO$_n$R, wherein n represents 1 or 2 and R represents aryl which is optionally substituted by one or more identical or different substituents from the group consisting of halogen, alkyl, alkenyl, halogenoalkyl, nitro, alkoxy, alkylmercapto, dialkylamino, carbalkoxy, carbamoyl, N-alkylcarbamoyl, N,N-dialkylcarbamoyl, halogenoalkoxy, halogenoalkylmercapto, alkylsulphonylamino, alkylsulphonyl, aryl, aryloxy, arylmercapto, acyloxy, acyl, sulphamoyl, N-alkylsulphamoyl, N,N-dialkylsulphamoyl, aralkyloxy, aralkylmercapto, acylamino, acylalkylamino, cycloalkyl and cyano.

3. A 4-halogeno-5-nitrothiazole according to claim 1, in which

Hal represents fluorine, chlorine, bromine or iodine, and

R represents alkyl having 1 to 12 carbon atoms, alkenyl having 3 to 12 carbon atoms, alkinyl having 4 to 12 carbon atoms or halogenoalkyl, halogenoalkenyl or halogenoalkinyl having in each case up to 8 carbon atoms and 1 to 10 identical or different halogen atoms, or represents alkoxyalkyl, alkylmercaptoalkyl or cyanoalkyl having 1 to 4 carbon atoms per alkyl part, or represents phenyloxyalkyl or phenylmercaptoalkyl having 1 to 4 carbon atoms in the alkyl part, it being possible for the phenyl radicals to be optionally substituted by one to three identical or different substituents from the group consisting of fluorine, chlorine, bromine and alkyl having 1 to 4 carbon atoms, or represents cycloalkyl having 3 to 8 carbon atoms and optionally substituted by one to three identical or different alkyl substituents having 1 to 4 carbon atoms, it being possible for the cycloalkyl ring to carry a fused-on ring, or represents phenylalkyl having 1 to 4 carbon atoms in the alkyl part and optionally substituted by one to five identical or different substituents from the group consisting of halogen, alkyl having 1 to 4 carbon atoms, halogenoalkyl having 1 to 4 carbon atoms and 1 to 8 identical or different halogen atoms, nitro, cyano, alkoxy having 1 to 4 carbon atoms and alkylmercapto having 1 to 4 carbon atoms, the alkyl part of the phenylalkyl optionally containing, as a substituent, a further phenyl radical which can optionally be substituted as described above, or represents phenyl which is optionally substituted by one to five identical or different substituents from the group consisting of halogen, nitro, alkyl having 1 to 12 carbon atoms, alkoxy, alkylmercapto, carbalkoxy, alkylsulphonylamino, alkylsulphonyl, sulphamoyl, N-alkylsulphamoyl, N,N-dialkylsulphamoyl, dialkylamino, carbamoyl, N-alkylcarbamoyl or N,N-dialkylcarbamoyl having in each case 1 to 4 carbon atoms per alkyl radical, alkenyl or alkinyl having up to 6 carbon atoms, halogenoalkyl, halogenoalkoxy or halogenoalkylmercapto having in each case 1 to 4 carbon atoms and 1 to 8 identical or different halogen atoms per radical listed, phenyl, phenoxy, phenylmercapto, acyloxy having 1 to 3 carbon atoms, acyl having 1 to 3 carbon atoms, phenylalkyloxy having 1 to 3 carbon atoms in the alkyl part, phenylalkylmercapto having 1 to 3 carbon atoms, acylamino having 1 to 3 carbon atoms, acylalkylamino having 1 to 3 carbon atoms per acyl and alkyl radical, cycloalkyl having 4 to 6 carbon atoms and cyano, or represents naphthyl.

4. A 4-halogeno-5-nitrothiazole according to claim 1, in which

Hal represents chlorine, bromine or iodine, and

R represents alkyl having 1 to 8 carbon atoms, alkenyl having 3 to 8 carbon atoms, alkinyl having 4 to 8 carbon atoms, cycloalkyl having 3 to 6 carbon atoms, cyanoalkyl having 1 to 3 carbon atoms in the alkyl part, or represents phenyl, benzyl, phenethyl or naphthyl, optionally substituted by one to five identical or different substituents from the group consisting of alkyl having 1 to 12 carbon atoms, alkenyl having up to 3 carbon atoms, fluorine, chlorine, bromine, iodine, trifluoromethyl, nitro, alkoxy having 1 to 4 carbon atoms, alkylmercapto having 1 to 4 carbon atoms, dialkylamino having 1 or 2 carbon atoms per alkyl radical, carbalkoxy having 1 or 2 carbon atoms, trifluoromethoxy, trifluoromethylmercapto, alkylsulphonylamino having 1 or 2 carbon atoms, alkylsulphonyl having 1 or 2 carbon atoms, phenyl, phenoxy, phenylmercapto, acetoxy, acetyl, sulphamoyl, N-alkylsulphamoyl having 1 or 2 carbon atoms, N,N-dialkylsulphamoyl having 1 or 2 carbon atoms per alkyl radical, carbamoyl, N-alkylcarbamoyl having 1 or 2 carbon atoms, N-N-dialkylcarbamoyl having 1 or 2 carbon atoms per alkyl radical benzyloxy, benzylmercapto, formylamino, formylmethylamino, acetylamino, cyclopentyl, cyclohexyl and cyano.

5. A compound according to claim 1, wherein such compound is 4-chloro-5-nitro-2-(4-methoxyphenoxy)-thiazole of the formula

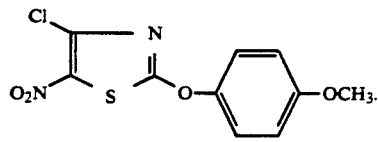

6. A compound according to claim 1, wherein such compound is 4-chloro-5-nitro-2-(4-nitrophenoxy)-thiazole of the formula

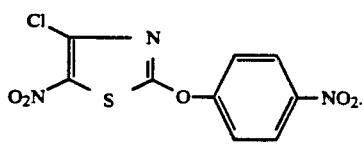

7. A compound according to claim 1, wherein such compound is 4-chloro-5-nitro-2-(4-fluorophenylmercapto)thiazole of the formula

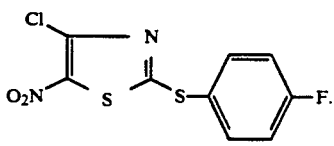

8. A compound according to claim 1, wherein such compound is 4-chloro-5-nitro-2-(2,3-dimethoxyphenoxy)thiazole of the formula

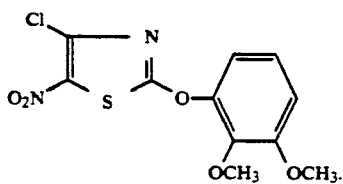

9. A fungicidal or microbicidal composition comprising a fungicidally or microbicidally effective amount of a compound according to claim 1 and a diluent.

10. A method of combating fungi or microbes which comprises applying to such fungi or microbes or to a fungus or microbe habitat a fungicidally or microbicidally effective amount of a compound according to claim 1.

11. The method according to claim 10, wherein such compound is
4-chloro-5-nitro-2-(4-methoxyphenoxy)-thiazole,
4-chloro-5-nitro-2-(4-nitrophenoxy)-thiazole,
4-chloro-5-nitro-2-(4-fluorophenylmercapto)-thiazole, or
4-chloro-5-nitro-2-(2,3-dimethoxyphenoxy)-thiazole.

* * * * *